(12) United States Patent
Diederich et al.

(10) Patent No.: US 6,383,151 B1
(45) Date of Patent: *May 7, 2002

(54) CIRCUMFERENTIAL ABLATION DEVICE ASSEMBLY

(76) Inventors: Chris J. Diederich, 19 Nova La., Novato, CA (US) 94945; Michael D. Lesh, 301 Monte Vista, Mill Valley, CA (US) 94941; James C. Peacock, III, 410 Winding Way, San Carlos, CA (US) 94070; Michael R. Ross, 1415 Marlborough, Hillsborough, CA (US) 94010

(*) Notice: Subject to any disclaimer, the term of this patent is extended or adjusted under 35 U.S.C. 154(b) by 0 days.

This patent is subject to a terminal disclaimer.

(21) Appl. No.: 09/659,477

(22) Filed: Sep. 11, 2000

Related U.S. Application Data

(63) Continuation of application No. 09/199,736, filed on Nov. 25, 1998, now Pat. No. 6,117,101, which is a continuation-in-part of application No. 08/889,798, filed on Jul. 8, 1997, now Pat. No. 6,024,740.
(60) Provisional application No. 60/073,527, filed on Feb. 3, 1998.

(51) Int. Cl.$^7$ ................................................. A61B 1/00
(52) U.S. Cl. ............................................................ 601/2
(58) Field of Search .................................. 600/373, 374, 600/381, 471, 585; 604/22, 101; 606/15, 32, 40, 41, 45, 46, 47, 48; 607/96, 99, 122; 601/2

(56) References Cited

U.S. PATENT DOCUMENTS 3,565,062 A 2/1971 Kuris (List continued on next page.)

FOREIGN PATENT DOCUMENTS

WO WO 93/20767 10/1993

(List continued on next page.)

Primary Examiner—George Manuel

(57) ABSTRACT

This invention is a circumferential ablation device assembly which is adapted to forming a circumferential conduction block in a pulmonary vein. The assembly includes a circumferential ablation element which is adapted to ablate a circumferential region of tissue along a pulmonary vein wall which circumscribes the pulmonary vein lumen, thereby transecting the electrical conductivity of the pulmonary vein against conduction along its longitudinal axis and into the left atrium. The circumferential ablation element includes an expandable member with a working length that is adjustable from a radially collapsed position to a radially expanded position. An equatorial band circumscribes the outer surface of the working length and is adapted to ablate tissue adjacent thereto when actuated by an ablation actuator. The equatorial band has a length relative to the longitudinal axis of the expandable member that is narrow relative to the working length, and is also substantially shorter than its circumference when the working length is in the radially expanded position. A pattern of insulators may be included over an ablation element which otherwise spans the working length in order to form the equatorial band described. The expandable member is also adapted to conform to the pulmonary vein in the region of its ostium, such as by providing a great deal of radial compliance or by providing a taper along the working length which has a distally reducing outer diameter. A linear ablation element is provided adjacent to the circumferential ablation element in a combination assembly which is adapted for use in a less-invasive "maze"-type procedure in the region of the pulmonary vein ostia in the left ventricle. A cylindrical ultrasound transducer is provided on an inner member within the balloon and forms the circumferential ablation member by emitting a radial ultrasound signal which is circumferential to the transducer and highly collimated to the transducer's length. The circumferential ultrasound signal sonically couples to the balloon's outer skin to form the circumferential ablation element that is adapted to ablate a circumferential path of tissue engaged to the balloon.

21 Claims, 21 Drawing Sheets

U.S. PATENT DOCUMENTS

| | | |
|---|---|---|
| 3,938,502 A | 2/1976 | Bom |
| 4,117,836 A | 10/1978 | Erickson |
| 4,316,472 A | 2/1982 | Mirowski et al. |
| 4,641,649 A | 2/1987 | Walinsky et al. |
| 4,660,571 A | 4/1987 | Hess et al. |
| 4,662,368 A | 5/1987 | Hussein et al. |
| 4,669,469 A | 6/1987 | Gifford, III et al. |
| 4,676,258 A | 6/1987 | Inokuchi et al. |
| 4,699,147 A | 10/1987 | Chilson et al. |
| 4,757,820 A | 7/1988 | Itoh |
| 4,762,129 A | 8/1988 | Bonzel |
| 4,841,977 A | 6/1989 | Griffith et al. |
| 4,882,777 A | 11/1989 | Narula |
| 4,924,863 A | 5/1990 | Sterzer |
| 4,936,281 A | 6/1990 | Stasz |
| 4,951,677 A | 8/1990 | Crowley et al. |
| 4,998,933 A | 3/1991 | Eggers et al. |
| 5,000,185 A | 3/1991 | Yock |
| 5,002,059 A | 3/1991 | Crowley et al. |
| 5,131,397 A | 7/1992 | Crowley |
| 5,156,157 A | 10/1992 | Valenta, Jr. et al. |
| 5,186,177 A | 2/1993 | O'Donnell et al. |
| 5,195,990 A | 3/1993 | Weldon |
| 5,209,229 A | 5/1993 | Gilli |
| 5,222,501 A | 6/1993 | Ideker et al. |
| 5,226,430 A | 7/1993 | Spears et al. |
| 5,228,442 A | 7/1993 | Imran |
| 5,231,996 A | 8/1993 | Desai |
| 5,281,215 A | 1/1994 | Milder |
| 5,292,321 A | 3/1994 | Lee |
| 5,293,868 A | 3/1994 | Nardella |
| 5,295,484 A | 3/1994 | Marcus et al. |
| 5,324,255 A | 6/1994 | Passafaro et al. |
| 5,324,284 A | 6/1994 | Imran |
| 5,325,860 A | 7/1994 | Seward et al. |
| 5,331,966 A | 7/1994 | Bennett et al. |
| 5,342,292 A | 8/1994 | Nita et al. |
| 5,345,940 A | 9/1994 | Seward et al. |
| 5,368,035 A | 11/1994 | Hamm et al. |
| 5,368,557 A | 11/1994 | Nita et al. |
| 5,368,558 A | 11/1994 | Nita |
| 5,372,138 A | 12/1994 | Crowley et al. |
| 5,385,148 A | 1/1995 | Lesh et al. |
| 5,391,197 A | 2/1995 | Burdette et al. |
| 5,409,000 A | 4/1995 | Imran |
| 5,411,524 A | 5/1995 | Rahul |
| 5,421,338 A | 6/1995 | Crowley et al. |
| 5,437,664 A | 8/1995 | Cohen et al. |
| 5,447,509 A | 9/1995 | Mills et al. |
| 5,454,373 A | 10/1995 | Koger et al. |
| 5,496,312 A | 3/1996 | Klicek |
| 5,496,346 A | 3/1996 | Horzewski et al. |
| 5,497,119 A | 3/1996 | Tedrow et al. |
| 5,501,227 A | 3/1996 | Yock |
| 5,509,900 A | 4/1996 | Lum et al. |
| 5,558,672 A | 9/1996 | Edwards et al. |
| 5,564,440 A | 10/1996 | Swartz et al. |
| 5,571,088 A | 11/1996 | Lennox et al. |
| 5,571,159 A | 11/1996 | Alt |
| 5,575,766 A | 11/1996 | Swartz et al. |
| 5,606,974 A | 3/1997 | Liang et al. |
| 5,620,479 A | 4/1997 | Diederich |
| 5,630,837 A | 5/1997 | Crowley |
| 5,681,308 A | 10/1997 | Edwards et al. |
| 5,685,839 A | 11/1997 | Edwards et al. |
| 5,687,723 A | 11/1997 | Avitall |
| 5,725,494 A | 3/1998 | Brisken |
| 5,728,062 A | 3/1998 | Brisken |
| 5,733,315 A | 3/1998 | Burdette et al. |
| 5,735,280 A | 4/1998 | Sherman et al. |
| 5,735,811 A | 4/1998 | Brisken |
| 5,749,880 A | 5/1998 | Banas et al. |
| 5,769,846 A | 6/1998 | Edwards et al. |
| 5,797,903 A | 8/1998 | Swanson et al. |
| 5,800,379 A | 9/1998 | Edwards et al. |
| 5,800,429 A | 9/1998 | Edwards |
| 5,824,046 A | 10/1998 | Smith et al. |
| 5,846,218 A | 12/1998 | Brisken et al. |
| 5,851,232 A | 12/1998 | Lois |
| 5,921,982 A | 7/1999 | Lesh et al. |
| 5,928,279 A | 7/1999 | Shannon et al. |
| 5,938,660 A | 8/1999 | Swartz et al. |
| 5,971,983 A | 10/1999 | Lesh |
| 6,001,093 A | 12/1999 | Swanson et al. |
| 6,090,084 A * | 7/2000 | Hassett ...................... 600/585 |
| 6,117,101 A | 9/2000 | Diederich et al. |
| 6,146,379 A | 11/2000 | Fleischman et al. |
| 6,161,543 A * | 12/2000 | Cox ........................... 606/41 |
| 6,214,002 B1 | 4/2001 | Fleischman et al. |

FOREIGN PATENT DOCUMENTS

| | | |
|---|---|---|
| WO | WO 93/20770 | 10/1993 |
| WO | WO 94/21165 | 9/1994 |
| WO | WO 95/19738 | 7/1995 |
| WO | WO 96/10961 | 4/1996 |
| WO | WO 96/32897 | 10/1996 |

* cited by examiner

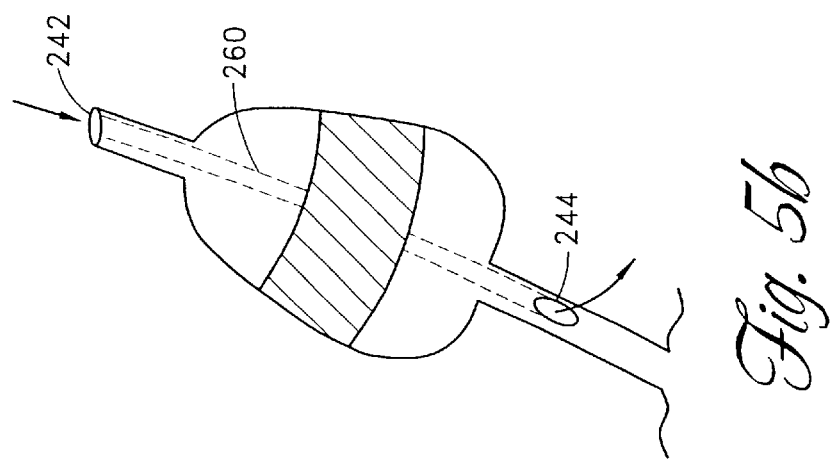
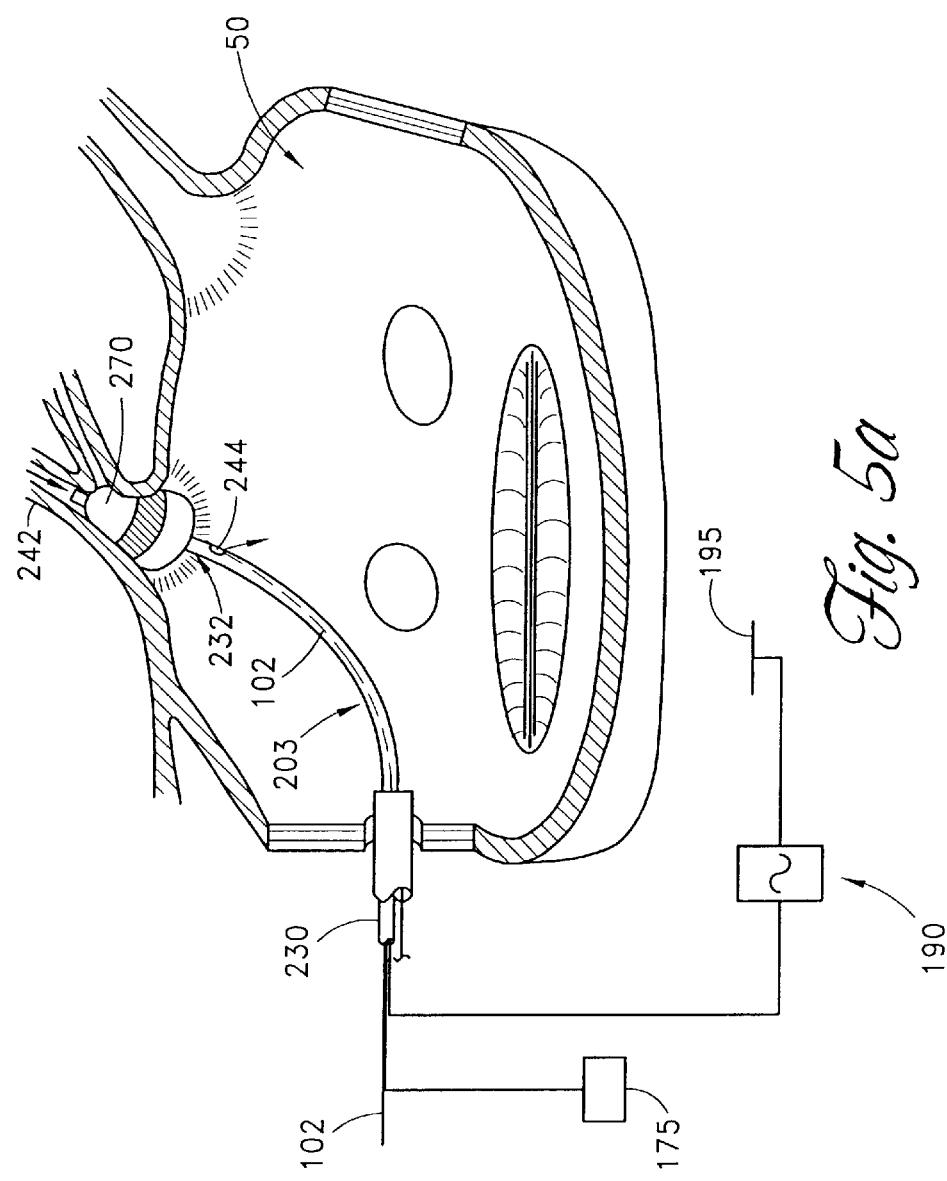
Fig. 5a
Fig. 5b

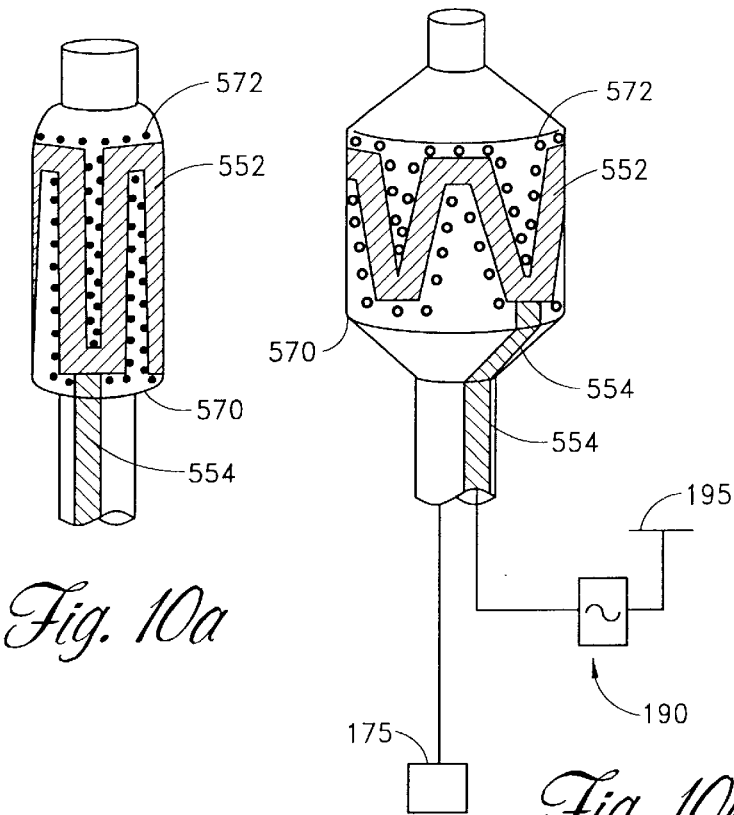
*Fig. 10a*
*Fig. 10b*
*Fig. 10c*
*Fig. 10d*
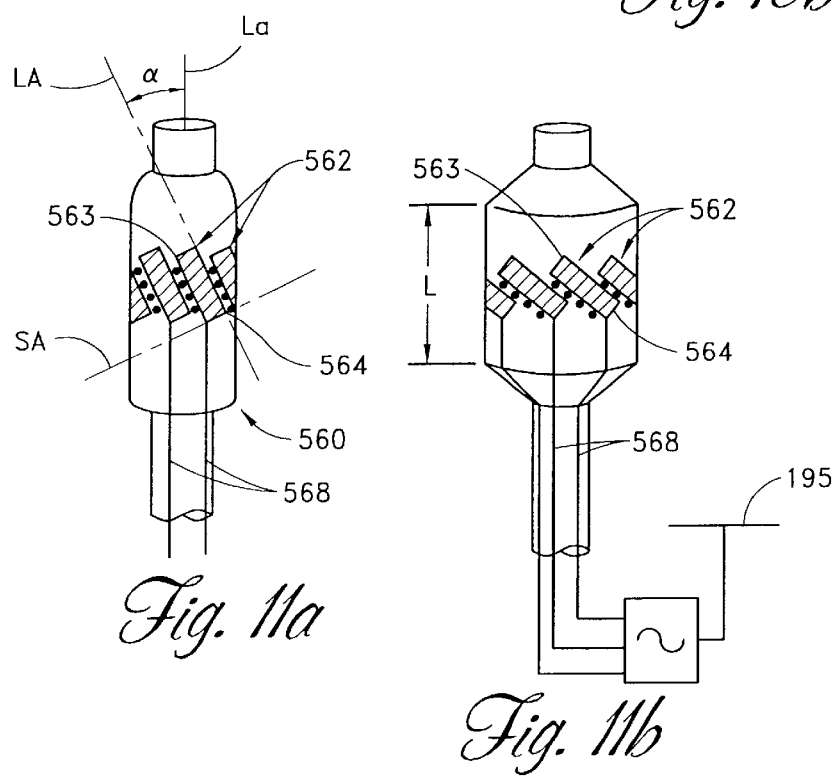
*Fig. 11a*
*Fig. 11b*

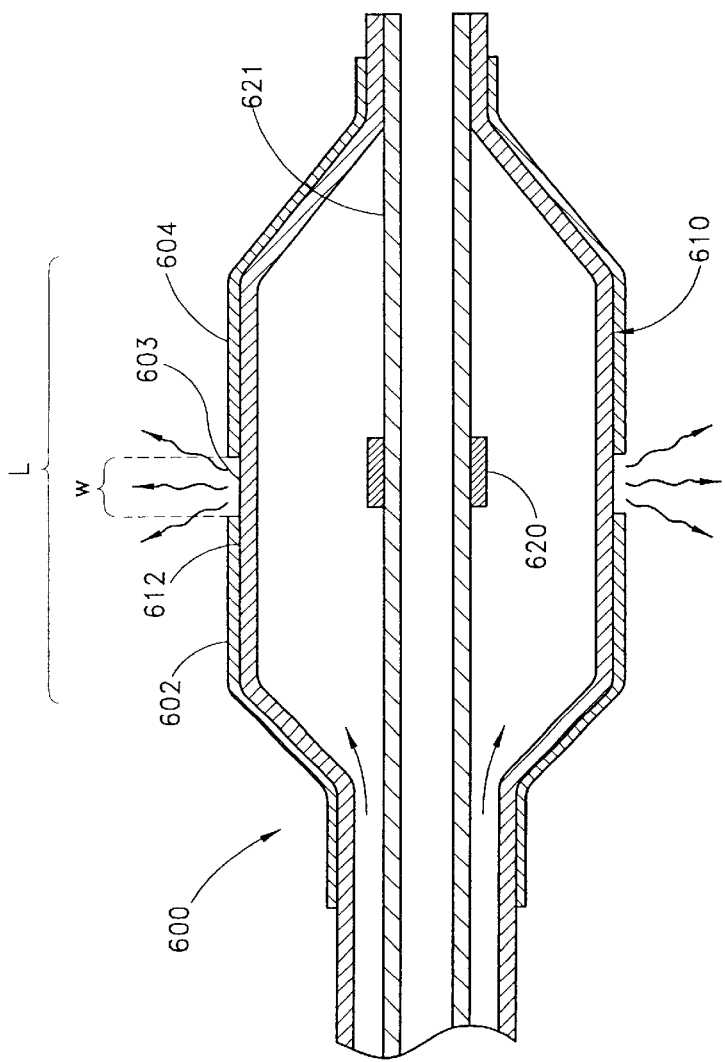
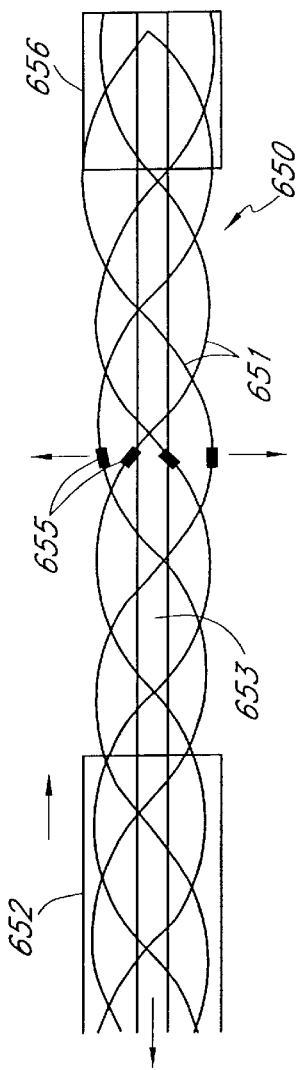
Fig. 12
Fig. 13

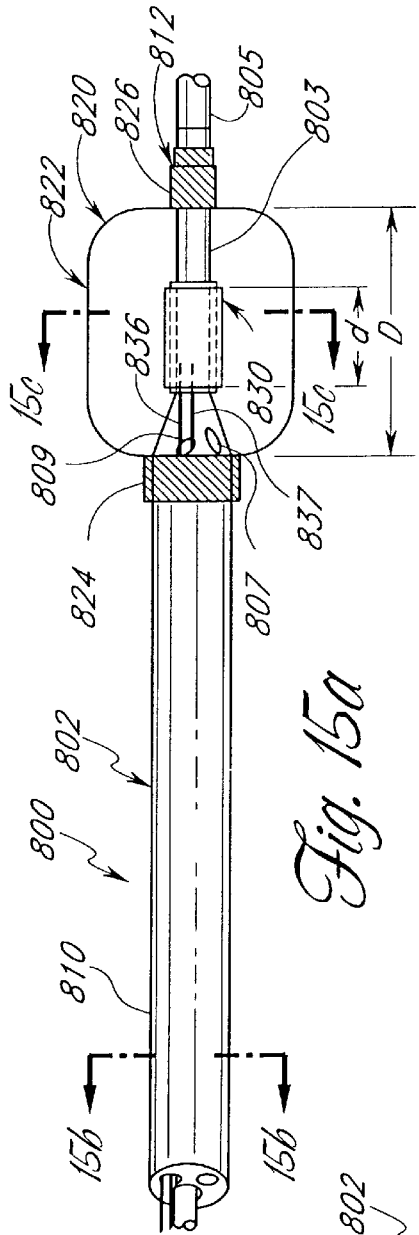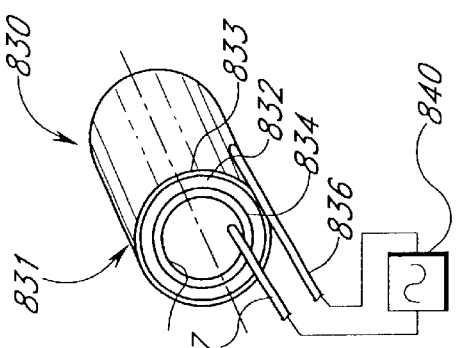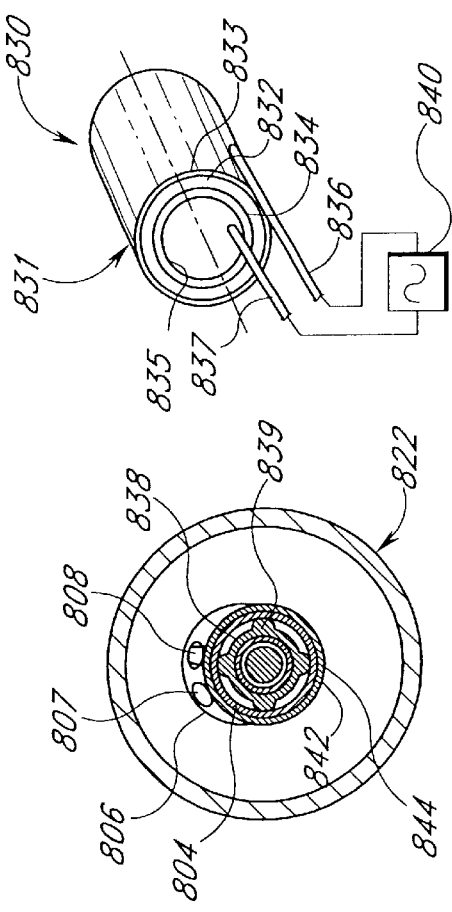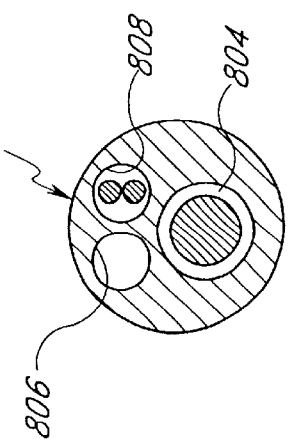

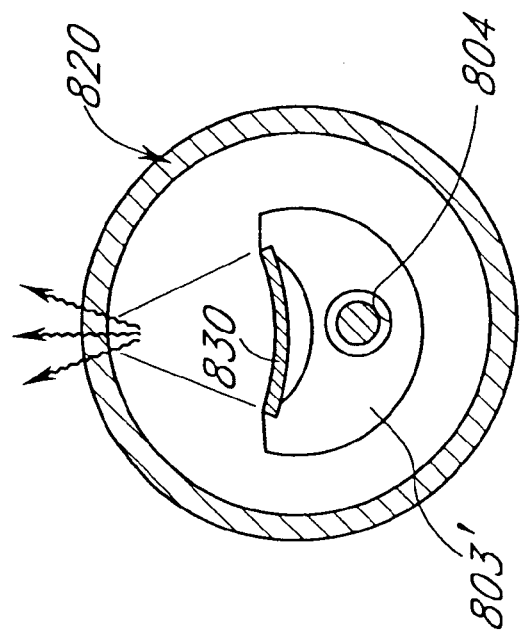
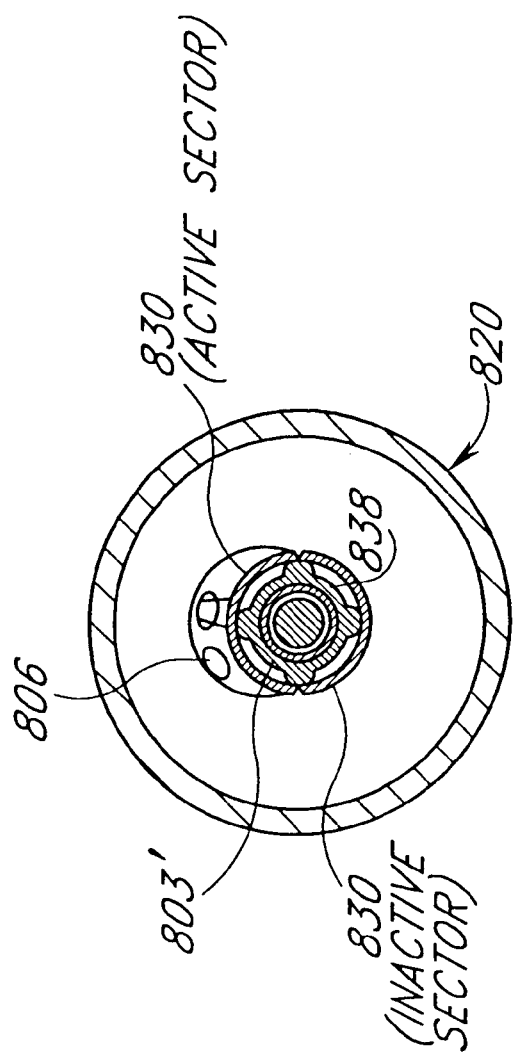

CIRCUMFERENTIAL ABLATION DEVICE ASSEMBLY

RELATED APPLICATIONS

This application is a continuation of U.S. patent application Ser. No. 09/199,736, filed on Nov. 25, 1998, now U.S. Pat. No. 6,117,101 which is a continuation-in-part of U.S. patent application Ser. No. 08/889,798, filed on Jul. 8, 1997, now U.S. Pat. No. 6,024,740, issued Feb. 15, 2000, to which this application claims priority under 35 U.S.C. §120. The present application claims the benefit of priority under 35 U.S.C. §119(e) of provisional application Ser. No. 60/073,527, filed on Feb. 3, 1998.

BACKGROUND OF THE INVENTION

1. Field of the Invention

The present invention is a surgical device. More specifically, it is a circumferential ablation device assembly which is adapted to ablate a selected circumferential region of tissue which is located either along a pulmonary vein wall, which forms a circumferential conduction block against conduction along the longitudinal axis of the pulmonary vein wall, or along a left posterior atrial wall which surrounds a pulmonary vein ostium and electrically isolates the vein and the ostium from the rest of the atrium.

2. Description of Related Art

Many abnormal medical conditions in humans and other mammals have been associated with disease and other aberrations along the lining or walls which define several different body spaces. In order to treat such abnormal wall conditions of the body spaces, medical device technologies adapted for delivering specific forms of ablative energy to specific regions of targeted wall tissue from within the associated body space have been developed and disclosed.

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

Atherosclerosis, a vascular disease characterized by abnormal deposits upon vessel walls or thickening thereof, is an example of an abnormal wall condition. The dangers related to flow blockages or functional occlusions resulting from the disease have made atherosclerosis the focus of many disclosed devices. Such devices can be categorized by their structures and tissue treatment mechanisms. These categories may include direct contact electrode devices, resistance heating devices, light transmission/conversion-to-heat devices, hot fluid lumen devices, and radio frequency (RF) heated devices.

Several direct (or nearly direct) contact electrode devices have been disclosed. U.S. Pat. No. 4,998,933 to Eggers et al. describes a catheter designed for thermal angioplasty which utilizes a heated electrode in direct contact with surrounding tissue or plaque deposits as a mechanism for treating the diseased lumen walls. U.S. Pat. No. 4,676,258 to InoKuchi et al. and U.S. Pat. No. 4,807,620 to Strul et al. disclose devices designed to treat surrounding tissues using heat generated by two electrodes within the device and an RF power source.

U.S. Pat. No. 4,672,962 to Hershenson and U.S. Pat. No. 5,035,694 to Kasprzyk et al. disclose devices which may be categorized as resistance heating probes. In each of these devices, current flowing through a conductive material at the end of the device provides heat which is transmitted to surrounding tissues for treatment of atherosclerosis and other diseases. Current is transmitted in each of these devices by electrically conductive materials. In contrast, U.S. Pat. No. 5,226,430 to Spears et al. discloses a device which uses light transmitting fiber to transmit energy to a heat generating element at the tip of the device. The heat generating element in that device transmits heat energy to a surrounding balloon structure which is in contact with surrounding tissue. In further contrast, U.S. Pat. No. 4,790,311 to Ruiz discloses an angioplasty catheter system wherein a heat generating electrode at the tip of the device is heated using the transmission of RF energy. This device may be categorized as an RF heated device.

U.S. Pat. Nos. 5,190,540 and 5,292,321 to Lee can be categorized as hot fluid lumen devices. In the '540 disclosure, Lee describes a balloon catheter designed for remodelling a body lumen. This device utilizes a multilumen catheter which is capable of delivering heated fluid to an expandable balloon lumen, thereby expanding the balloon geometrically and heating tissue which is in contact with the balloon. In the '321 disclosure, Lee describes a similar device wherein the lumen of an expandable balloon is filled with thermoplastic material which is designed to become softer and more moldable when heated by a heating element.

Endometriosis, another abnormal wall tissue condition, is associated with the endometrial cavity of the female. This medical condition, characterized by dangerously proliferative uterine wall tissue along the surface of the endometrial cavity, has been treated by delivering energy to the tissue. U.S. Pat. No. 5,449,380 to Chin discloses a medical device for delivering energy to the wall tissue of a diseased endometrial cavity using a balloon lumen with heated fluid circulating therein. Other devices, such as those disclosed in U.S. Pat. No. 5,505,730 to Edwards; U.S. Pat. No. 5,558,672 to Edwards et al. and U.S. Pat. No. 5,562,720 to Stern et al. are designed for treating particular tissues using heat generated by the flow of RF current between electrodes.

Diseased or structurally damaged blood vessels may bring about various abnormal wall conditions. The inducement of thrombosis and control of hemorrhaging within certain body lumens such as vessels have been the focus of several disclosed devices which use catheter-based heat sources for cauterizing damaged tissues. In U.S. Pat. No. 4,449,528, for example, Auth et al. disclose a thermal cautery probe designed for heating specific layers of tissue without producing deep tissue damage. The mechanism of heat generation in this device is a resistive coil within the cautery probe which is electrically connected to a power source. In U.S. Pat. No. 4,662,368, Hussein et al. disclose a device designed for localized heat application within a lumen. In this device, energy for heat generation is delivered to the tip of the device in the form of light by a flexible fiber. Heat from an element which converts light energy to heat energy is then conducted to the adjacent tissue. In U.S. Pat. No. 4,522,205, Taylor et al. disclose a device designed for inducing thrombosis in a blood vessel comprising an array of electrodes mounted onto an expandable balloon which may be delivered by a catheter. The inventors of this device hypothesize that when direct current flows through electrodes which are in contact with adjacent tissues, thrombosis is precipitated.

Maintenance of patency in diseased lumens such as blood vessels has been the focus of several disclosed devices, several of which may be characterized as cardiovascular stents. U.S. Pat. No. 5,078,736 to Behl, for example, discloses an apparatus for maintaining patency in the body passages comprising a stent structure which may be connected to a radiofrequency power source. In addition to mechanically supporting a body lumen, this device may provide for thermal disruption of the adjacent tissues which may inhibit reocclusion of the lumen. U.S. Pat. No. 5,178,618 to Kandarpa discloses a similar device which may be used for recanalizing an occluded vessel prior to mechanically supporting a lumen region.

Atrial Fibrillation

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. No. 4,641,649 to Walinsky et al. and WO 96/32897 to Desai.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Conventional Atrial Arrhythmia Treatments

Several pharmacological approaches intended to remedy or otherwise treat atrial arrhythmias have been disclosed, such as, for example, in U.S. Pat. No. 4,673,563 to Berne et al.; U.S. Pat. No. 4,569,801 to Molloy et al.; and also by Hindricks, et al. in "Current Management of Arrhythmias" (1991). However, such pharmacological solutions are not generally believed to be entirely effective in many cases, and may in some cases result in proarrhythmia and long term inefficacy.

Several surgical approaches have also been developed with the intention of treating atrial fibrillation. One particular example is known as the "maze procedure," as is disclosed by Cox, J L et al. in "The surgical treatment of atrial fibrillation. I. Summary" *Thoracic and Cardiovascular Surgery* 101(3), pp. 402–405 (1991); and also by Cox, J L in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

While the "maze" procedure as reported by Cox and others, and also other surgical procedures, have met some success in treating patients with atrial arrhythmia, its highly invasive methodology is believed to be prohibitive in most cases. However, these procedures have provided a guiding principle that mechanically isolating faulty cardiac tissue may successfully prevent atrial arrhythmia, and particularly atrial fibrillation caused by perpetually wandering reentrant wavelets or focal regions of arrhythmogenic conduction.

Modern Catheter Treatments for Atrial Arrhythmia

Success with surgical interventions through atrial segmentation, particularly with regard to the surgical "maze" procedure just described, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as are disclosed in the following U.S. patents: U.S. Pat. No. 5,617,854 to Munsif; U.S. Pat. No. 4,898,591 to Jang et al.; U.S. Pat. No. 5,487,385 to Avitall; and U.S. Pat. No. 5,582,609 to Swanson. The disclosures of these patents are herein incorporated in their entirety by reference thereto.

Additional examples of catheter-based tissue ablation in performing less-invasive cardiac chamber segmentation procedures are also disclosed in the following articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al.,*Journal of Cardiovascular Electrophysiology* 7(12), pp. 1132–1144 (1996). These articles are herein incorporated in their entirety by reference thereto.

Furthermore, the use of particular guiding sheath designs for use in ablation procedures in both the right and/or left atrial chambers are disclosed in U.S. Pat. Nos. 5,427,119; 5,497,119; 5,564,440; 5,575,766 to Swartz et al. In addition, various energy delivery modalities have been disclosed for forming such atrial wall lesions, and include use of microwave, laser, and more commonly, radiofrequency energies to create conduction blocks along the cardiac tissue wall, as disclosed in WO 93/20767 to Stern et al.; U.S. Pat. No. 5,104,393 to Isner et al.; and U.S. Pat. No. 5,575,766 to Swartz et al, respectively. The disclosures of these references are herein incorporated in their entirety by reference thereto.

In addition to attempting atrial wall segmentation with long linear lesions for treating atrial arrhythmia, ablation catheter devices and methods have also been disclosed which are intended to ablate arrhythmogenic tissue of the left-sided accessory pathways, such as those associated with the Wolff-Parkinson-White syndrome, through the wall of an adjacent region along the coronary sinus.

For example, Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995), disclose attempted thermal ablation of left-sided accessory pathways in dogs using a balloon which is heated with bipolar radiofrequency electrodes positioned within the balloon. A 10 French guiding catheter and a 0.035" wire were provided in an assembly adapted to advance the ablation catheter into the coronary sinus from the jugular vein. Thermal ablation procedures were performed in the posterospetal coronary sinus and in the left free-wall coronary sinus with thermal inflations at either 70 deg, 80 deg, or 90 deg for either 30 or 60 seconds. In all cases balloon occlusion was confirmed using distal dye injection. A compliant silicone balloon was used which had a diameter range of 5–20 mm and a length range of 8–23 mm over a final inflation pressure range of 0.4 to 1.5 atms. Fram et al. discloses that the lesion depth of some population groups may be sufficient to treat patients with Wolff-Parkinson-White syndrome.

Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger C D et al., *Circulation* (1992) 86:947–954; and "Percutaneous laser balloon coagulation of accessory pathways", McMath L P et al., Diagn Ther Cardiovasc Interven 1991; 1425:165–171.

Focal Arrhythmias Originating from Pulmonary Veins

Atrial fibrillation may be focal in nature, caused by the rapid and repetitive firing of an isolated center within the atrial cardiac muscle tissue. These foci, defined by regions exhibiting a consistent and centrifugal pattern of electrical activation, may act as either a trigger of atrial fibrillatory paroxysmal or may even sustain the fibrillation. Recent studies have suggested that focal arrhythmia often originates from a tissue region along the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways.

One example of a focal ablation method intended to destroy and thereby treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre, et al. disclose radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and were ablated using a standard 4 mm tip single ablation electrode.

In another focal ablation example, Jais et al. in "A focal source of atrial fibrillation treated by discrete radiofrequency ablation" *Circulation* 95:572–576 (1997) applies an ablative technique to patients with paroxysmal arrhythmias originating from a focal source. At the site of arrhythmogenic tissue, in both right and left atria, several pulses of a discrete source of radiofrequency energy were applied in order to eliminate the fibrillatory process.

None of the cited references discloses a circumferential ablation device assembly which is adapted to form a circumferential conduction block around the circumference of a pulmonary vein wall in order to treat focal left atrial arrhythmias originating in the pulmonary vein.

Nor do the cited references disclose a circumferential ablation device with a circumferential ablation element that forms an equatorial band along the working length of an expandable element which has a length that is substantially less that the working length of the expandable element.

Nor do the cited references disclose a circumferential ablation device with an expandable member which has a shape when expanded that is adapted to conform to a pulmonary vein ostium along a left ventricular wall.

Nor do the cited references disclose a circumferential ablation device with an ablation element which circumscribes a radially compliant expandable element and which is adapted to form a continuous circumferential lesion in tissue over a working range of expanded diameters.

Nor do the cited references disclose a circumferential ablation device assembly that includes a circumferential ablation element on an expandable member and also a linear lesion ablation element adjacent to the expandable member.

Nor do the cited references disclose a circumferential ablation device assembly that includes only one a cylindrical ultrasound transducer which is positioned within an expandable balloon and which is ultrasonically coupled to a circumferential band of the balloon's skin to form an equatorial banded ablation element which is adapted to form a circumferential conduction block along a pulmonary vein.

Nor do the cited references disclose a circumferential ablation device assembly which includes a cylindrical ultrasound transducer which is positioned within an expandable balloon that is adapted, when adjusted to a radially expanded condition, to engage a pulmonary vein such that the cylindrical ultrasound transducer is positioned and is ultrasonically coupled to a circumferential band of the balloon's skin that circumscribes the ostium of the vein.

SUMMARY OF THE INVENTION

The present invention is a circumferential ablation device assembly which is adapted to form a circumferential lesion along a circumferential path of tissue along a body space wall and which circumscribes a body space defined at least in part by the body space. The assembly includes an elongate body, an expandable member on the distal end portion of the elongate body which is adjustable from a radially collapsed position to a radially expanded position, and a circumferential ablation element that includes an equatorial or other circumferential band which circumscribes at least a portion of an outer surface of the working length of the expandable member when in the radially expanded position. The circumferential ablation element is adapted to ablate a circumferential region of tissue adjacent to the equatorial band and along the body space wall when the circumferential ablation element is coupled to and actuated by an ablation actuator.

In one variation, the equatorial band length is shorter than two-thirds the working length of the expandable member. In one mode of this variation, the ablation element includes a circumferential RF electrode in an RF ablation circuit. In another mode, the circumferential ablation electrode includes a porous membrane along the equatorial or other circumferential band which is adapted to pass electrically conductive fluid from the conductive fluid chamber and into tissue adjacent to the band, the fluid conducting current to the tissue in an RF ablation circuit. In still another mode, a thermal conductor is located along the equatorial band and is adapted to emit thermal energy into tissue adjacent to the equatorial band when the thermal conductor is coupled to and actuated by a thermal ablation actuator. In still a further mode, a pair of insulators may be positioned exteriorly of each of two ends of the circumferential ablation element, wherein the uninsulated space between the insulators forms the equatorial band which may be equatorially located or otherwise circumferentially located.

In another variation of the invention, a circumferential ablation member includes an expandable member with a working length which, when adjusted from a radially collapsed position to a radially expanded position, is adapted to conform to a pulmonary vein ostium. In one mode of this variation, the working length when expanded includes a taper with a distally reducing outer diameter from a proximal region to a distal region. In a further mode, the expandable member is radially compliant and is adapted to conform to the pulmonary vein ostium when the working length is expanded to the radially expanded position in the left atrium and the expandable member is thereafter forced retrogradedly against the pulmonary vein wall in the region of the pulmonary vein ostium.

In another variation of the invention, a circumferential ablation member includes an expandable member with a working length which is adjustable between a plurality of radially expanded positions each having a different expanded outer diameters in the region of the equatorial band. The equatorial band of the circumferential ablation element is adapted to ablate a continuous circumferential lesion pattern in tissue surrounding the equatorial band over the range of expanded outer diameters. In one mode of this variation, the equatorial band has a secondary shape along the outer surface of the working length, such as a modified step, serpentine, or sawtooth shape.

In another variation, the distal end portion of an elongate member includes a circumferential ablation member and also a linear ablation member having an elongate ablation element length and linear ablation element which is adapted to form a continuous linear lesion in tissue adjacent thereto when the linear ablation element is coupled to an ablation actuator. In a further mode of this variation, a first end of the linear ablation member is located adjacent to the expandable member which forms at least in part a first anchor adapted to secure the first linear ablation member end in the region of a pulmonary vein ostium along a left atrium wall. A second anchor is also provided adjacent to a second, opposite end of the linear ablation member end and is adapted to secure the second linear ablation member end to a second location along the left atrium wall.

In a further mode of the invention, a circumferential ablation device assembly includes a cylindrical ultrasound transducer which forms a circumferential ablation member that is adapted to form the circumferential conduction block. The transducer is positioned within a balloon and is sonically coupled to a circumferential region of the balloon's working length to thereby form a circumferential ablation element that circumscribes the outer surface of the balloon. The assembly is adapted to position the circumferential ablation element adjacent to a circumferential region of tissue along a pulmonary vein in the region of its ostium, and is further adapted to ablate that circumferential region of tissue with ultrasonic energy emitted from the transducer and coupled to the region of tissue via the circumferential ablation element.

In one aspect of this mode, the balloon is adapted to conform to the pulmonary vein ostium such that the circumferential ablation element is engaged to the circumferential region of tissue. In one variation of this aspect, the balloon is highly compliant and is adapted to expand to a radially expanded position which conforms to the pulmonary vein ostium. In another variation of this aspect, the balloon has a predetermined shape when expanded to the radially expanded condition and which is adapted to conform to the pulmonary vein ostium. Further to this variation, the predetermined shape may include a distally reducing tapered outer diameter along the working length of the balloon, and may still further include a pear shape with a contoured region along that taper.

In another aspect of this mode, only one cylindrical ultrasound transducer is provided within the balloon and is adapted to form the circumferential ablation member.

In another aspect of this mode, the balloon includes a filter which is adapted to adjust either the amount or pattern of the ultrasound energy which is transmitted to the tissue from the transducer.

In another aspect of this mode, the balloon has a predetermined shape which defines at least in part the pattern by which the transducer is sonically coupled to the balloon skin to form the circumferential ablation element.

BRIEF DESCRIPTION OF THE DRAWINGS

These and other features of the invention will now be described with reference to the drawings of preferred embodiments which are intended to illustrate and not to limit the invention.

FIG. 5A shows a similar perspective view as shown in FIG. 4, although showing a further circumferential ablation catheter variation which is adapted to allow for blood perfusion from the pulmonary vein and into the atrium while performing the circumferential ablation method shown diagrammatically in FIG. 2.

FIG. 5B is an enlarged partial view of the circumferential ablation catheter shown in FIG. 5A, with a perfusion lumen shown in phantom.

FIGS. 7A–B show perspective views of another circumferential ablation catheter variation during use in a left atrium according to the method of FIG. 2, wherein FIG. 7A shows a radially compliant expandable member with a working length adjusted to a radially expanded position while in the left atrium, and FIG. 7B shows the expandable member after advancing it into and engaging a pulmonary vein ostium while in the radially expanded position.

FIGS. 10A–B show perspective views of one circumferential ablation member variation for use in the circumferential ablation device assembly of the present invention, showing a circumferential ablation electrode circumscribing the working length of an expandable member with a secondary shape along the longitudinal axis of the working length which is a modified step shape, the expandable member being shown in a radially collapsed position and also in a radially expanded position, respectively.

FIGS. 10C–D show perspective views of two circumferential ablation electrodes which form equatorial or otherwise circumferentially placed bands that circumscribe the working length of an expandable member and that have serpentine and sawtooth secondary shapes, respectively, relative to the longitudinal axis of the expandable member when adjusted to a radially expanded position.

FIGS. 11A–B show perspective views of another circumferential ablation element which includes a plurality of individual ablation electrodes that are spaced circumferentially to form an equatorial band which circumscribes the working length of an expandable member either in an equatorial location or an otherwise circumferential location that is bounded both proximally and distally by the working length, and which are adapted to form a continuous circumferential lesion while the working length is adjusted to a radially expanded position.

FIG. 12 shows a cross-sectional view of another circumferential ablation member for use in the circumferential ablation device assembly according to the present invention, wherein the circumferential ablation element circumscribes an outer surface of an expandable member substantially along its working length and is insulated at both the proximal and the distal ends of the working length to thereby form an uninsulated equatorial band in a middle region of the working length or otherwise circumferential region of the working length which is bounded both proximally and distally by end portions of the working length, which member is adapted to ablate a circumferential path of tissue in a pulmonary wall adjacent to the equatorial band.

FIG. 13 shows a perspective view of another circumferential ablation member which is adapted for use in the circumferential ablation device assembly of the present invention, wherein the expandable member is shown to be a cage of coordinating wires which are adapted to be adjusted from a radially collapsed position to a radially expanded position in order to engage electrode elements on the wires about a circumferential pattern of tissue in a pulmonary vein wall.

FIG. 15A shows a longitudinal cross-sectional view of another circumferential ablation catheter according to the present invention, and shows the ablation element to include a single cylindrical ultrasound transducer which is positioned along an inner member within an expandable balloon which is further shown in a radially expanded condition.

FIG. 15B shows a transverse cross-sectional view of the circumferential ablation catheter shown in FIG. 15A taken along line 15B—15B shown in FIG. 15A.

FIG. 15C shows a transverse cross-sectional view of the circuferential ablation catheter shown in FIG. 15A taken along line 15C—15C shown in FIG. 15A.

FIG. 15D shows a perspective view of the ultrasonic transducer of FIG. 15A in isolation.

FIG. 15E shows a modified version of the ultrasonic transducer of FIG. 15D with individually driven sectors.

FIG. 18A shows a transverse cross-sectional view of an additional circumferential ablation catheter according to the present invention, and shows the ablation element to include a single transducer sector segment which is positioned along an inner member within an expandable balloon which is further shown in a radially expanded condition.

FIG. 18B shows a transverse cross-sectional view of an a further circumferential ablation catheter according to the present invention, and shows the ablation element to include a single curvilinear section that is mounted so as to position its concave surface facing in a radially outward direction.

DETAILED DESCRIPTION OF THE PREFERRED EMBODIMENTS

As will be described with reference to the detailed embodiments below, the present invention is a circumferential ablation device assembly which is adapted to treat patients with atrial arrhythmia by forming a circumferential conduction block in a pulmonary vein which blocks electrical conduction along the longitudinal axis of the pulmonary vein wall and into the left atrium.

The terms "circumference" or "circumferential", including derivatives thereof, are herein intended to mean a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be, for example, circular, oblong, ovular, elliptical, or otherwise planar enclosures. A circumferential path may also be three dimensional, such as, for example, two opposite-facing semi-circular paths in two different parallel or off-axis planes which are connected at their ends by line segments bridging between the planes.

Figure 1A:
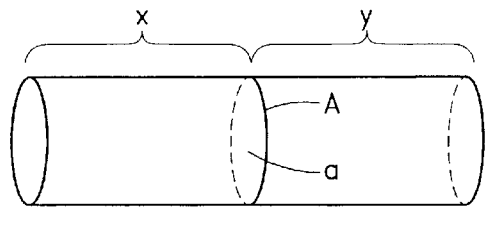
FIGS. 1A–E show schematic, perspective views of various exemplary circumferential conduction blocks formed in pulmonary vein wall tissue with the circumferential ablation device assembly of the present invention.
Figure 1B:
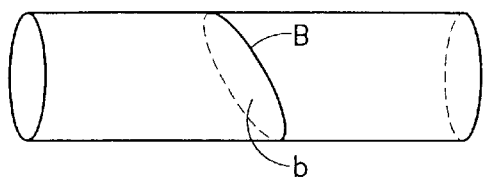
Figure 1C:
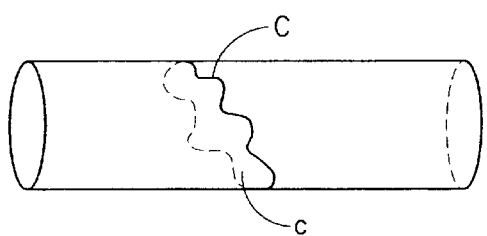
Figure 1D:
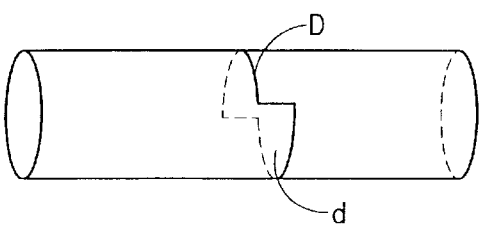
Figure 1E:
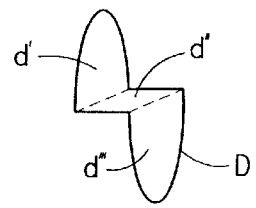

For purpose of further illustration, FIGS. 1A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 1D, FIG. 1E shows an exploded perspective view of circumferential path D as it circumscribes multiplanar portions of the pulmonary vein lumen shown at d', d", and d''', which together make up region d as shown in FIG. 1D.

The term "transect", including derivatives thereof, is also herein intended to mean to divide or separate a region of space into isolated regions. Thus, each of the regions circumscribed by the circumferential paths shown in FIGS. 1A–D transects the respective pulmonary vein, including its lumen and its wall, to the extent that the respective pulmonary vein is divided into a first longitudinal region located on one side of the transecting region, shown, for example, at region "X" in FIG. 1A, and a second longitudinal region on the other side of the transecting plane, shown, for example, at region "Y" also in FIG. 1A.

Therefore, a "circumferential conduction block" according to the present invention is formed along a region of tissue which follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryoblation element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that tissue.

The term "diagnose", including derivatives thereof, is intended to include patients suspected or predicted to have atrial arrhythmia, in addition to those having specific symptoms or mapped electrical conduction indicative of atrial arrhythmia.

In one aspect of using the circumferential ablation device assembly of the present invention, a patient diagnosed with multiple wavelet arrhythmia originating from multiple regions along the atrial wall is treated in part by forming the circumferential conduction block as an adjunct to forming long linear regions of conduction block between adjacent pulmonary vein ostia in a less-invasive "maze"-type catheter ablation procedure. More detail regarding particular ablation catheter embodiments adapted for use in such a method is provided below with reference to a combination circumferential-long linear lesion ablation device which is described below with reference to FIGS. 8A–D.

A patient diagnosed with focal arrhythmia originating from an arrhythmogenic origin or focus in a pulmonary vein may also be treated with the circumferential ablation device assembly of the present invention by using the assembly to form a circumferential conduction block along a circumferential path of pulmonary vein wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

Figure 2:
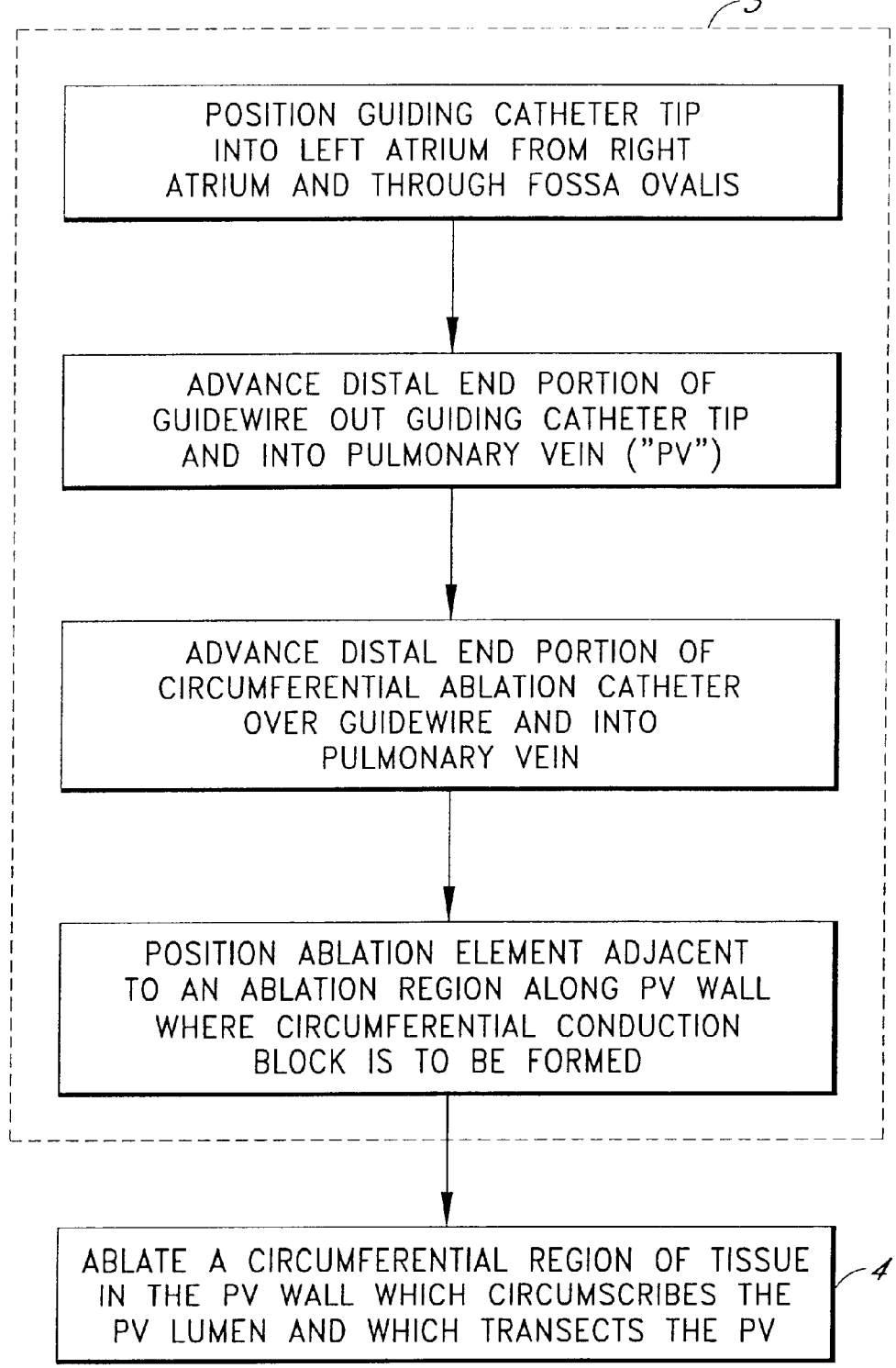
FIG. 2 shows a flow diagram of a method for using the circumferential ablation device assembly of the present invention.

FIG. 2 diagrammatically shows the sequential steps of a method for using the circumferential ablation device assembly of the present invention in forming a circumferential conduction block in a pulmonary vein. The circumferential ablation method according to FIG. 2 includes: positioning a circumferential ablation element at an ablation region along the pulmonary vein according to a series of detailed steps shown collectively in FIG. 2 as positioning step (3); and thereafter ablating a continuous circumferential region of tissue in the PV wall at the ablation region according to ablation step (4).

Further to positioning step (3) according to the method of FIG. 2, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes for using the circumferential ablation device assembly of the present invention. In one alternative variation not shown, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to gaining transeptal access to the left atrium as just described, positioning step (3) according to FIG. 2 next includes advancing a guidewire into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) which is coaxial within the guiding catheter, such as, for example, by using one of the directional catheters disclosed in U.S. Pat. No. 5,575,766 to Swartz. Or, the guidewire may have sufficient stiffness and maneuverability in the left atrial cavity to unitarily subselect the desired pulmonary vein distally of the guiding catheter seated at the fossa ovalis.

Suitable guidewire designs for use in the overall circumferential ablation device assembly of the present invention may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" may be suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity.

Subsequent to gaining pulmonary vein access, positioning step (3) of FIG. 2 next includes tracking the distal end portion of a circumferential ablation device assembly over the guidewire and into the pulmonary vein, followed by positioning a circumferential ablation element at an ablation region of the pulmonary vein where the circumferential conduction block is to be desirably formed.

Figure 3:
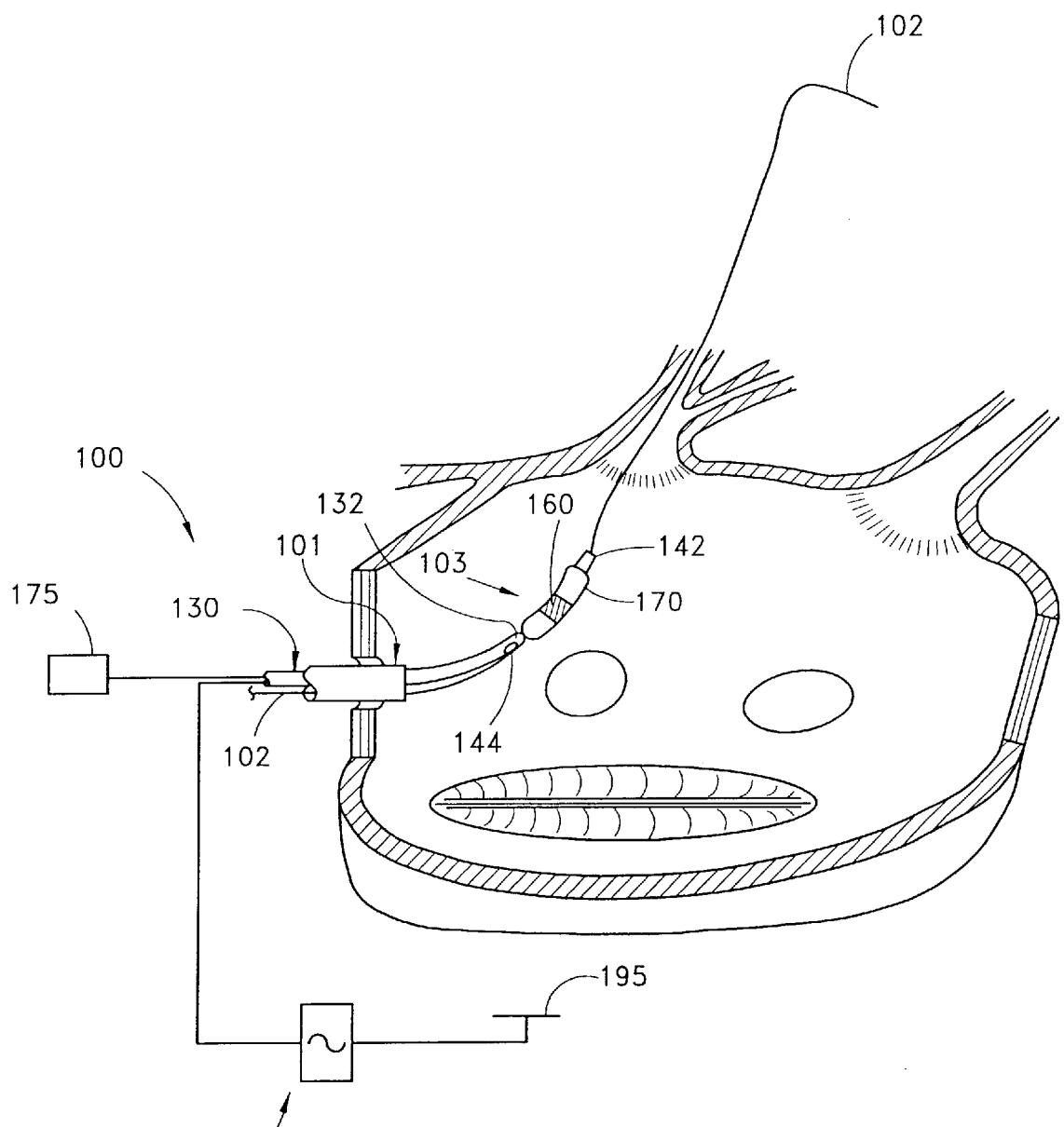
FIG. 3 shows a perspective view of a circumferential ablation device assembly during use in a left atrium subsequent to performing transeptal access and guidewire positioning steps according to the method of FIG. 2.
Figure 4:
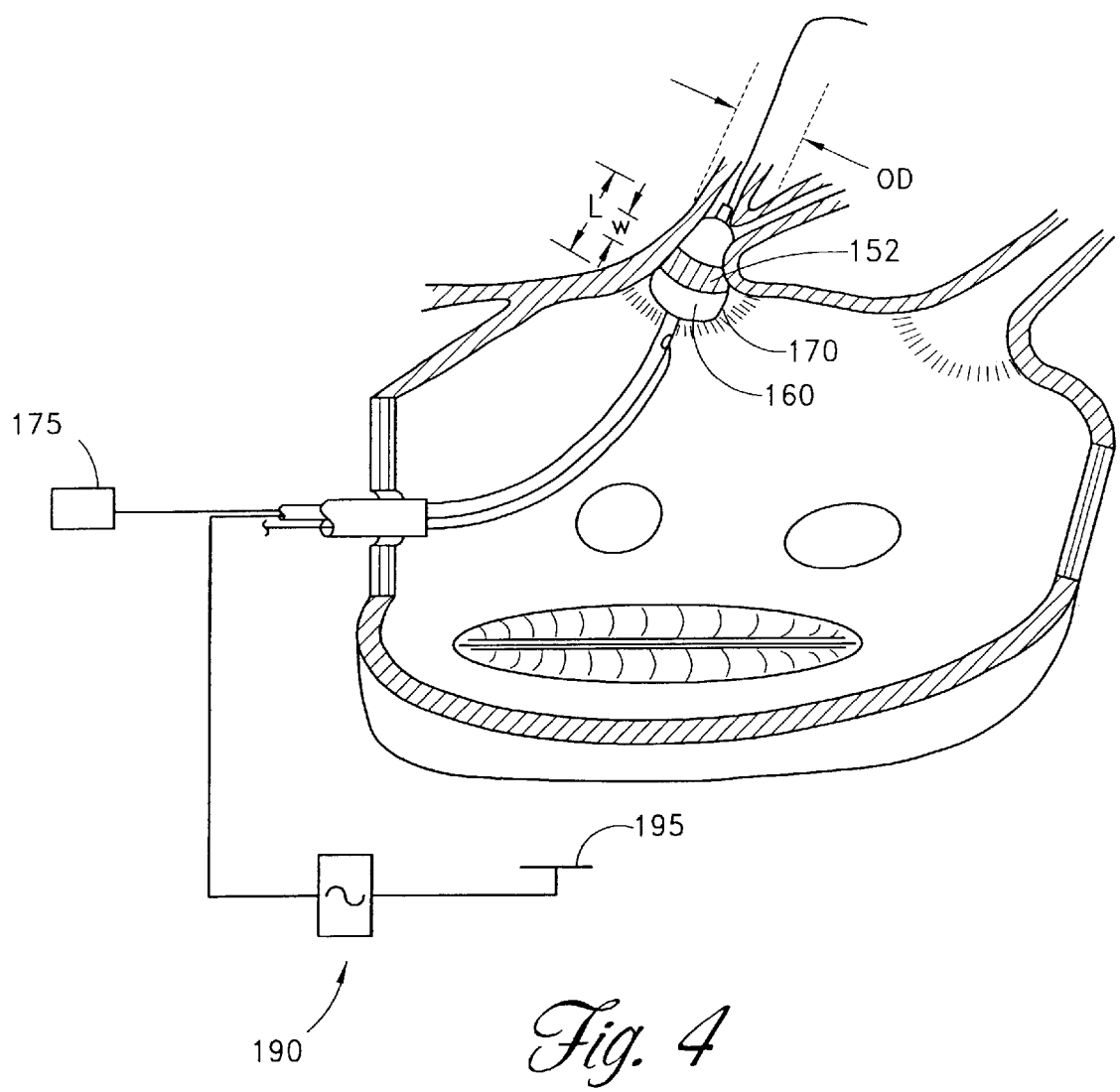
FIG. 4 shows a similar perspective view of the circumferential ablation device assembly shown in FIG. 3, and further shows a circumferential ablation catheter during use in ablating a circumferential region of tissue along a pulmonary vein wall to form a circumferential conduction block in the pulmonary vein according to the method of FIG. 2.

FIGS. 3–4 further show a circumferential ablation device assembly (100) according to the present invention during use in performing positioning step (3) and ablation step (4) just described with reference to FIG. 2. Included in the circumferential ablation device assembly (100) are guiding catheter (101), guidewire (102), and circumferential ablation catheter (103).

More specifically, FIG. 3 shows guiding catheter (101) subsequent to performing a transeptal access method according to FIG. 2, and also shows guidewire (102) subsequent to advancement and positioning within a pulmonary vein, also according to step (3) of FIG. 2. FIG. 3 shows circumferential ablation catheter (103) as it tracks coaxially over guidewire (102) with a distal guidewire tracking member, which is specifically shown only in part at first and second distal guidewire ports (142,144) located on the distal end portion (132) of an elongate catheter body (130). A guidewire lumen (not shown) extends between the first and second distal guidewire ports (142,144) and is adapted to slideably receive and track over the guidewire. In the particular variation of FIG. 3, the second distal guidewire port (142) is located on a distal end portion (132) of the elongate catheter body (130), although proximally of first distal guidewire port (142).

As would be apparent to one of ordinary skill, the distal guidewire tracking member shown in FIG. 3 and just described may be slideably coupled to the guidewire externally of the body in a "backloading" technique after the guidewire is first positioned in the pulmonary vein. Furthermore, there is no need in this guidewire tracking variation for a guidewire lumen in the proximal portions of the elongate catheter body (130), which allows for a reduction in the outer diameter of the catheter shaft in that region.

Nevertheless, it is further contemplated that a design which places the second distal guidewire port on the proximal end portion of the elongate catheter body would also be acceptable, as is described below, for example, with reference to the perfusion embodiment of FIG. 5.

In addition, the inclusion of a guidewire lumen extending within the elongate body between first and second ports, as provided in FIG. 3, should not limit the scope of acceptable guidewire tracking members according to the present invention. Other guidewire tracking members which form a bore adapted to slideably receive and track over a guidewire are also considered acceptable, such as, for example, the structure adapted to engage a guidewire as described in U.S. Pat. No. 5,505,702 to Arney, the entirety of which is hereby incorporated by reference herein.

While the assemblies and methods shown variously throughout the Figures include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixed-wire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

FIG. 3 also shows circumferential ablation catheter (103) with a circumferential ablation element (160) formed on an expandable member (170). The expandable member (170) is shown in FIG. 3 in a radially collapsed position adapted for percutaneous translumenal delivery into the pulmonary vein according to positioning step (3) of FIG. 2. However, expandable member (170) is also adjustable to a radially expanded position when actuated by an expansion actuator (175), as shown in FIG. 4. Expansion actuator (175) may include, but is not limited to, a pressurizeable fluid source. According to the expanded state shown in FIG. 4, expandable member (170) includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation element (160) also includes a circumferential band (152) on the outer surface of working length L which is coupled to an ablation actuator (190) at a proximal end portion of the elongate catheter body (shown schematically). After expandable member (170) is adjusted to the radially expanded position and at least a portion of working length L circumferentially engages the pulmonary vein wall in the ablation region, the circumferential band (152) of the circumferential ablation element (160) is actuated by ablation actuator (190) to ablate the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

FIG. 5A shows another circumferential ablation catheter (203) during use also according to the method of FIG. 2, wherein a perfusion lumen (260) (shown in phantom in FIG. 5B) is formed within the distal end portion (232) of elongate catheter body (230). The perfusion lumen (260) in this example is formed between a distal perfusion port, which in this example is the first distal guidewire port (242), and proximal perfusion port (244). Proximal perfusion port (244) is formed through the wall of the elongate catheter body (230) and communicates with the guidewire lumen (not shown) which also forms the perfusion lumen between the distal and proximal perfusion ports. In the particular design shown, after the guidewire has provided for the placement of the ablation element into the pulmonary vein, the guidewire is withdrawn proximally of the proximal perfusion port (244) (shown schematically in shadow) so that the lumen between the ports is clear for antegrade blood flow into the distal perfusion port (242), proximally along the perfusion lumen, out the proximal perfusion port (244) and into the atrium (perfusion flow shown schematically with arrows).

Further to the perfusion design shown in FIGS. 5A–B, guidewire (102) is positioned in a guidewire lumen which extends the entire length of the elongate catheter body (230) in an "over-the-wire"-type of design, which facilitates the proximal withdrawal of the guidewire to allow for perfusion while maintaining the ability to subsequently readvance the guidewire distally through the first distal guidewire port (242) for catheter repositioning. In one alternative variation not shown, the guidewire is simply withdrawn and disengaged from the second distal guidewire port (244), in which case the circumferential ablation catheter must generally be withdrawn from the body in order to recouple the distal guidewire tracking member with the guidewire.

In another alternative perfusion variation not shown which is a modification of the embodiment of FIG. 5A, a proximal perfusion port is provided as a separate and distinct port positioned between the second distal guidewire port (244) and the expandable member (270), which allows for proximal withdrawal of the guidewire to clear the guidewire lumen and thereby form a perfusion lumen between the first distal guidewire port and the proximal perfusion port. The guidewire of this alternative variation, however, remains engaged within the guidewire lumen between the second distal guidewire port and the proximal perfusion port.

Passive perfusion during expansion of the expandable member is believed to minimize stasis and allow the target pulmonary vein to continue in its atrial filling function during the atrial arrhythmia treatment procedure. Without this perfusion feature, the expandable member when in the radially expanded position during ablation blocks the flow from the vein into the atrium, which flow stasis may result in undesirable thrombogenesis in the pulmonary vein distally to the expandable member. In addition, in cases where the ablation element is adapted to ablate tissue with heat conduction at the ablation region, as described by reference to more detailed embodiments below, the perfusion feature according to the variation of FIGS. 5A–B may also provide a cooling function in the surrounding region, including in the blood adjacent to the expandable member.

Moreover, in addition to the specific perfusion structure shown and described by reference to FIGS. 5A–B, it is to be further understood that other structural variants which allow for perfusion flow during expansion of the expandable element may provide suitable substitutes according to one of ordinary skill without departing from the scope of the present invention.

Figure 6:
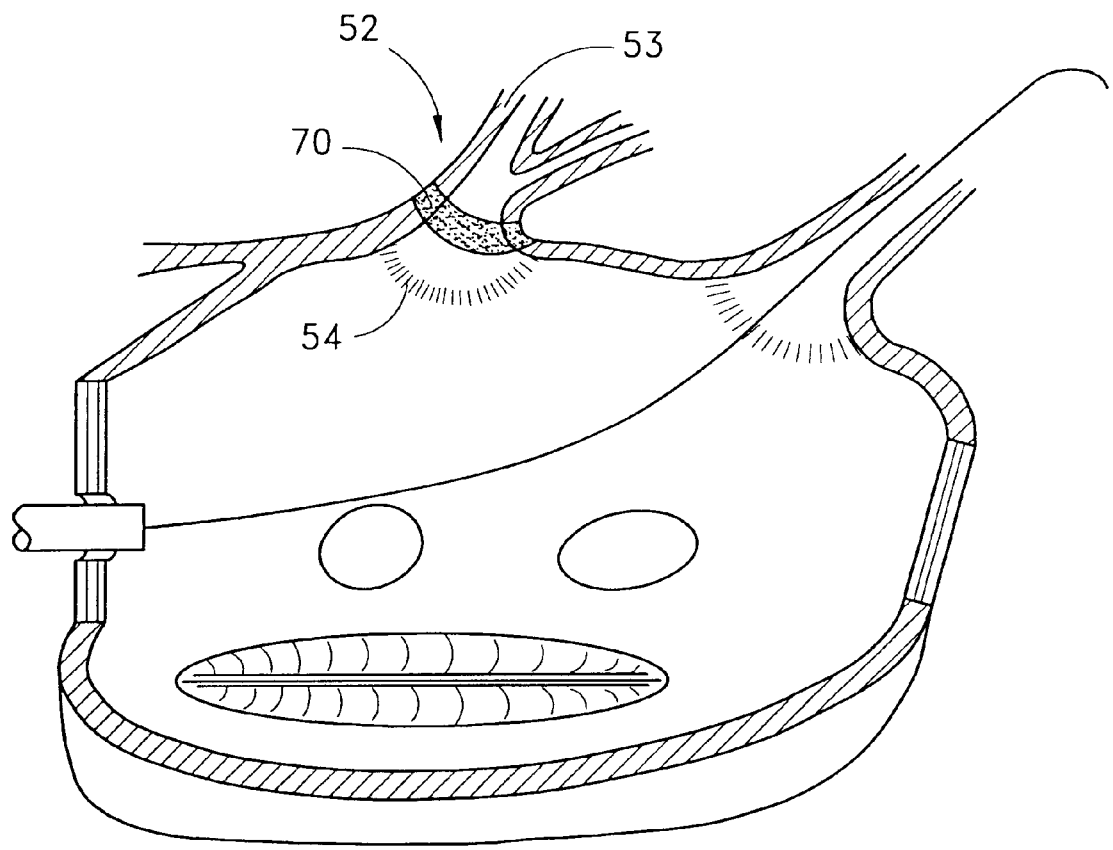
FIG. 6 shows a similar perspective view of the left atrium as that shown in FIGS. 3–5, although showing a cross-sectional view of a circumferential lesion after being formed by circumferential catheter ablation according to the method of FIG. 2.

FIG. 6 shows pulmonary vein (52) after removing the circumferential ablation device assembly subsequent to forming a circumferential lesion (70) around the ablation region of the pulmonary vein wall (53) according to the use of the circumferential ablation device assembly shown in stepwise fashion in FIGS. 3–6. Circumferential lesion (70) is shown located along the pulmonary vein adjacent to the pulmonary vein ostium (54), and is shown to also be "transmural," which is herein intended to mean extending completely through the wall, from one side to the other. Also, the circumferential lesion (70) is shown in FIG. 6 to form a "continuous" circumferential band, which is herein intended to mean without gaps around the pulmonary vein wall circumference, thereby circumscribing the pulmonary vein lumen.

It is believed, however, that circumferential catheter ablation with a circumferential ablation element according to the present invention may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 7A:
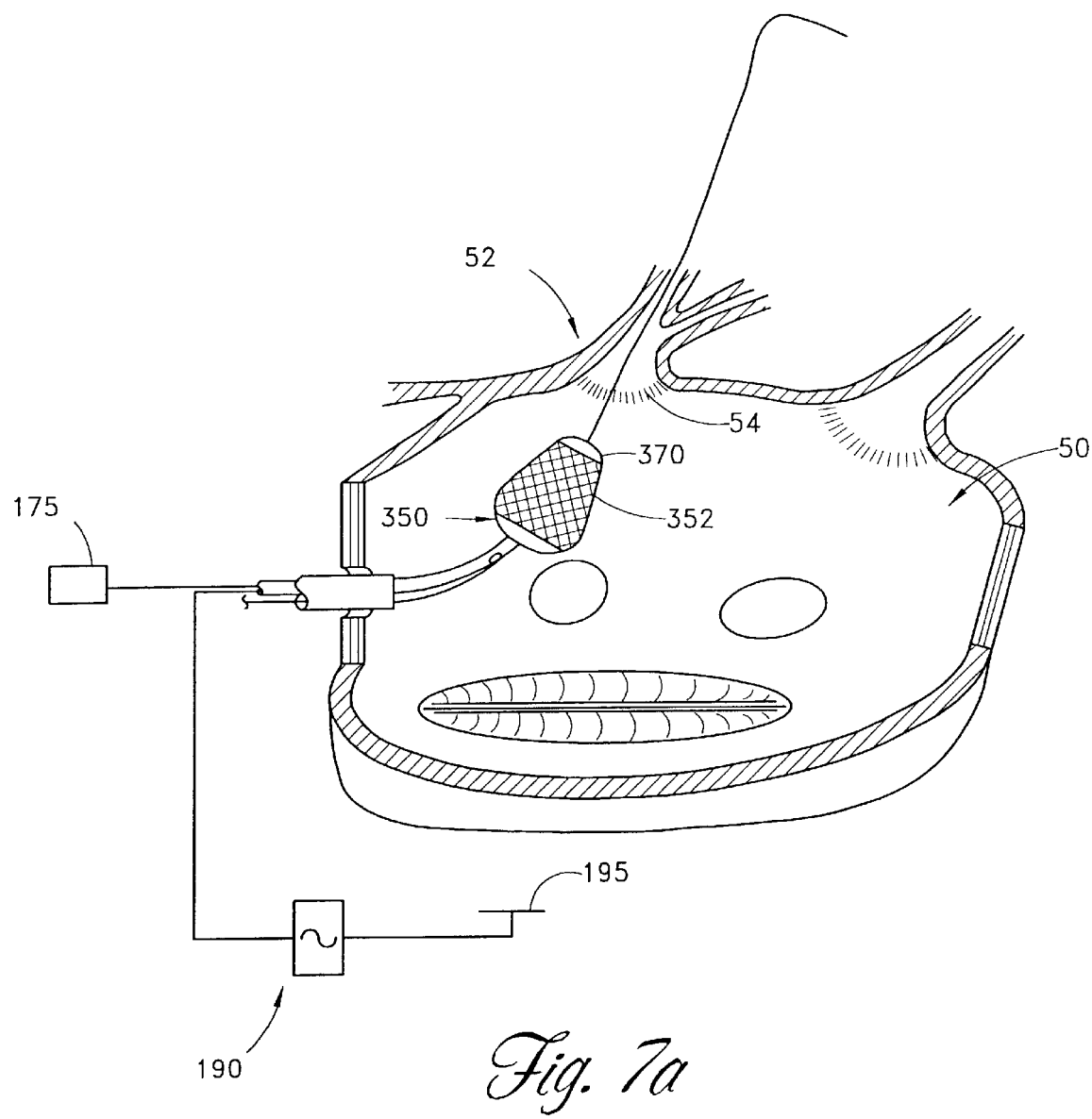
Figure 7B:
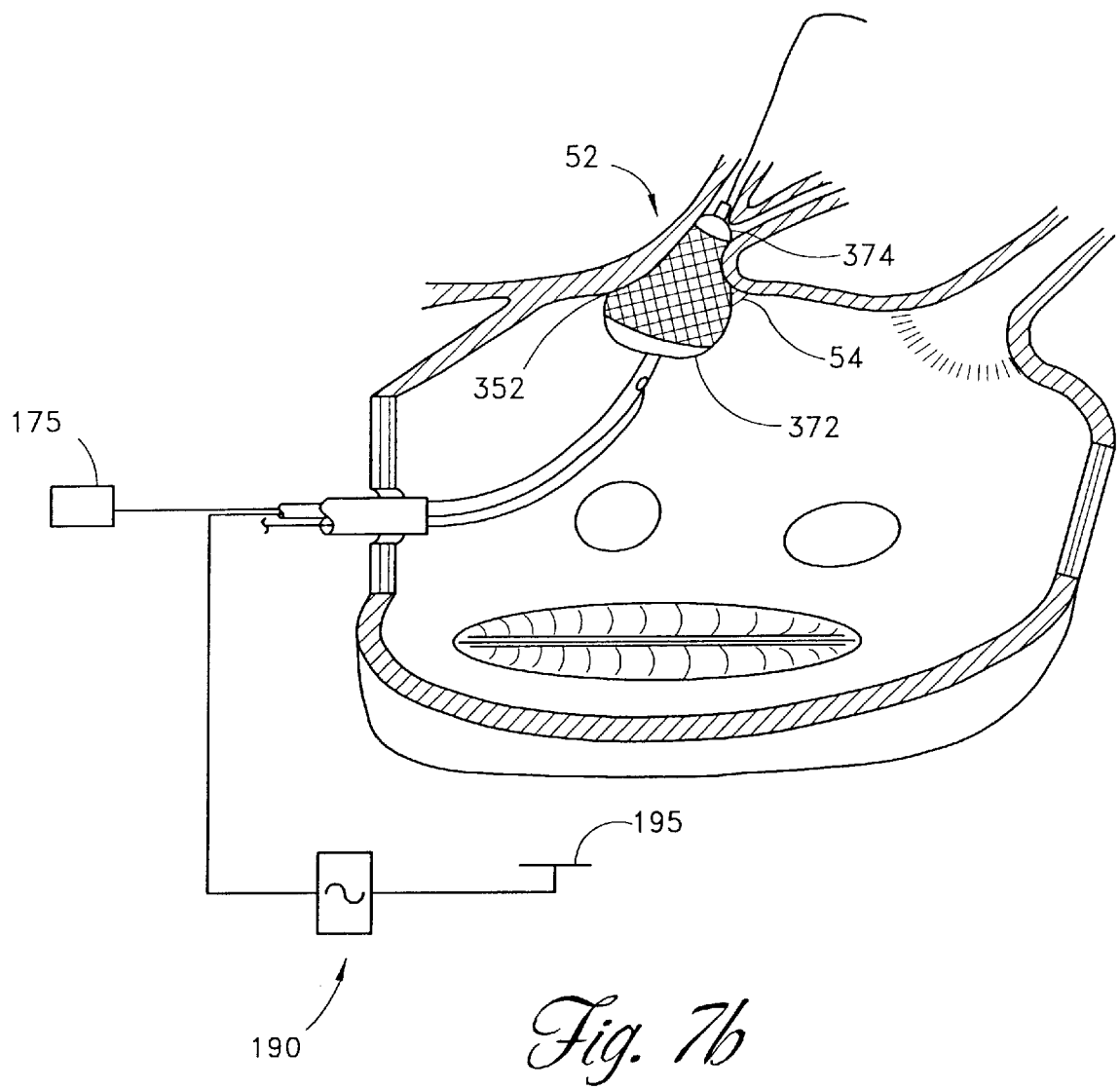
Figure 7C:
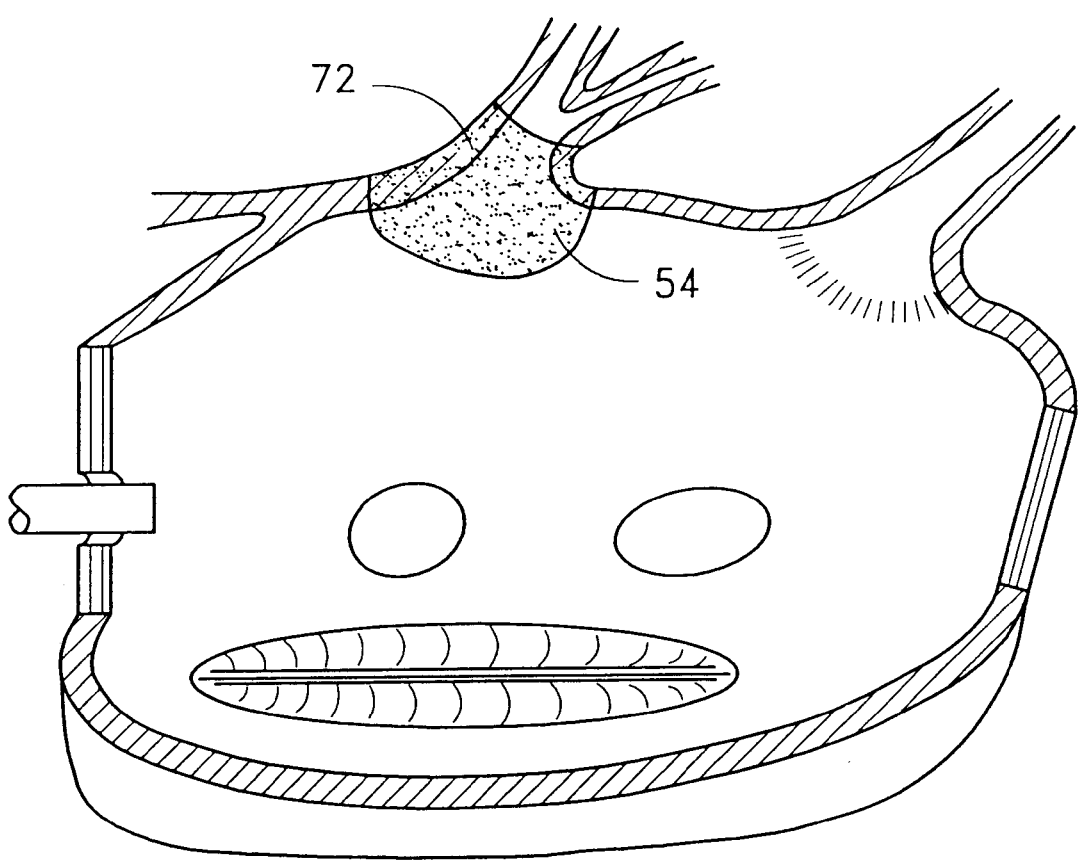
FIG. 7C shows the same perspective view of the left atrium shown in FIGS. 7A–B, although shown after forming a circumferential conduction block according to the circumferential ablation procedure of FIG. 2 and also after removing the circumferential ablation device assembly from the left atrium.

FIGS. 7A–B show a further variation of the present invention, wherein a circumferential ablation member (350) includes a radially compliant expandable member (370) which is adapted to conform to a pulmonary vein ostium (54) at least in part by adjusting it to a radially expanded position while in the left atrium and then advancing it into the ostium. FIG. 7A shows expandable member (370) after being adjusted to a radially expanded position while located in the left atrium (50). FIG. 7B further shows expandable member (370) after being advanced into the pulmonary vein (52) until at least a portion of the expanded working length L of circumferential ablation member (350), which includes a circumferential band (352), engages the pulmonary vein ostium (54). FIG. 7C shows a portion of a circumferential lesion (72) which forms a circumferential conduction block in the region of the pulmonary vein ostium (54) subsequent to actuating the circumferential ablation element to form the circumferential lesion.

FIGS. 8A–D collectively show a circumferential ablation device assembly according to the present invention as it is used to form a circumferential conduction block adjunctively to the formation of long linear lesions in a less-invasive "maze"-type procedure, as introduced above for the treatment of multiwavelet reentrant type fibrillation along the left atrial wall.

Figure 8A:
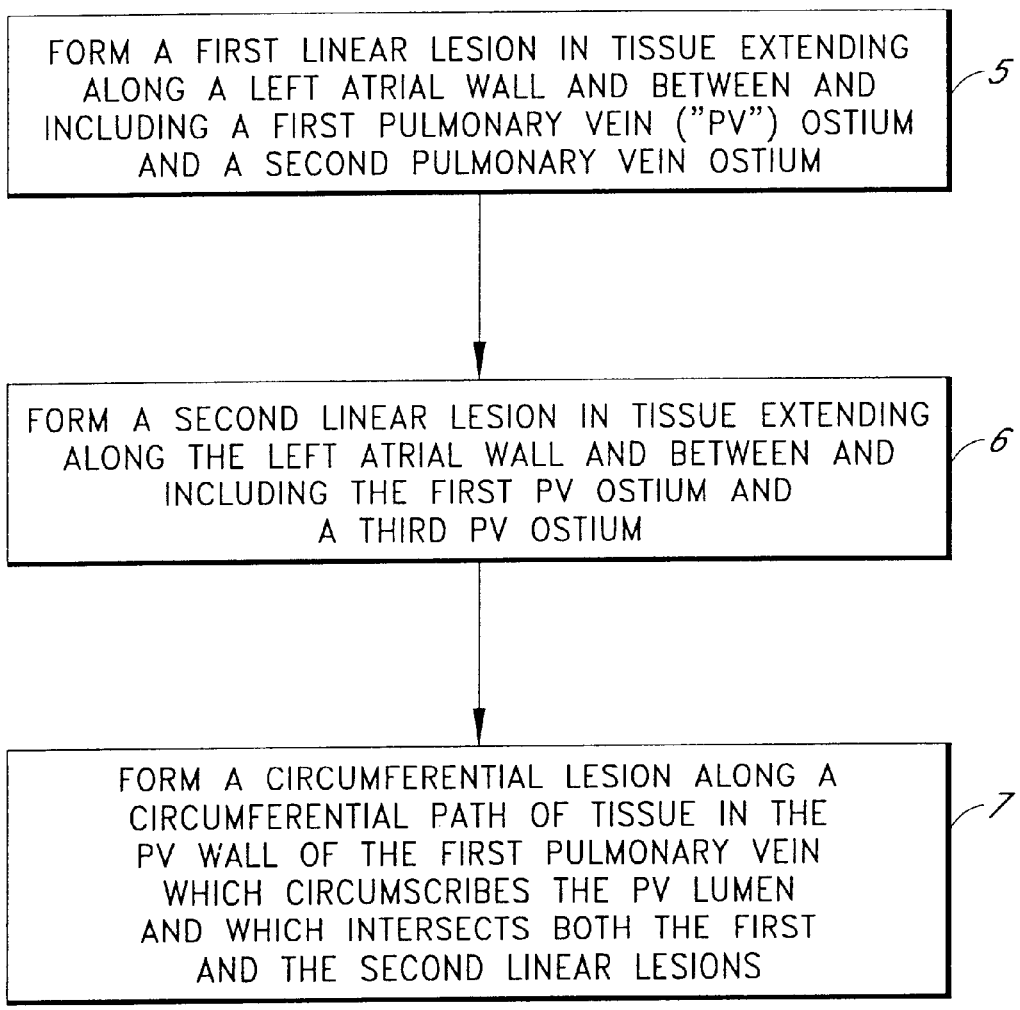
FIG. 8A diagrammatically shows a method for using the circumferential ablation device assembly of the present invention by forming a circumferential conduction block in a pulmonary vein in combination with a method for forming long linear lesions between pulmonary vein ostia in a less-invasive "maze"-type procedure.

More specifically, FIG. 8A diagrammatically shows a summary of steps for performing a "maze"-type procedure by forming circumferential conduction blocks that intersect with long linear conduction blocks formed between the pulmonary veins. As disclosed in copending patent application(Application Number not yet assigned) entitled "Tissue Ablation Device and Method of Use" filed by Michael Lesh, M.D. on May 9, 1997, which is herein incorporated in its entirety by reference thereto, a box-like conduction block surrounding an arrhythmogenic atrial wall region bounded by the pulmonary veins may be created by forming long linear lesions between anchors in all pairs of adjacent pulmonary vein ostia, such as is shown in part in steps (5) and (6) of FIG. 8A. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box, such as is shown between linear lesions (57,58) in FIG. 8B. Therefore, by forming the circumferential conduction block according to step (7) of FIG. 8A, and as shown by use of circumferential ablation member (450) in FIG. 8C, the linear lesions are thereby bridged and the gaps are closed.

Figure 8B:
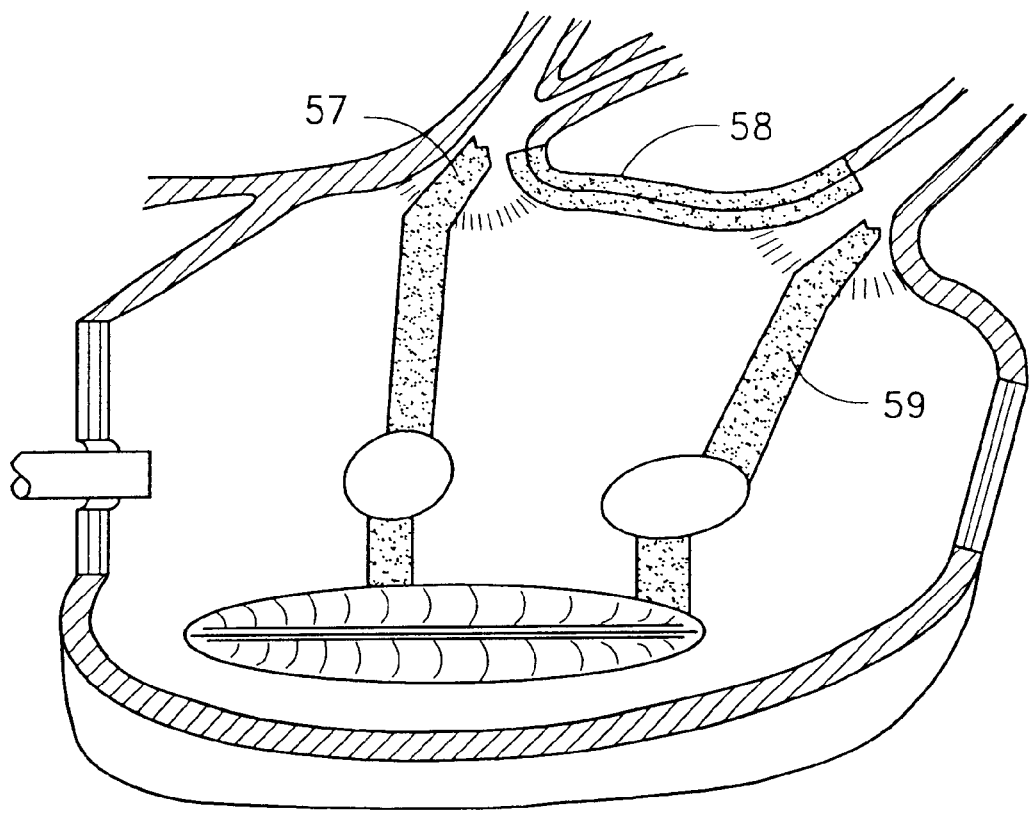
FIG. 8B shows a perspective view of a segmented left atrium after forming several long linear lesions between adjacent pairs of pulmonary vein ostia according to the method of FIG. 8A.
Figure 8C:
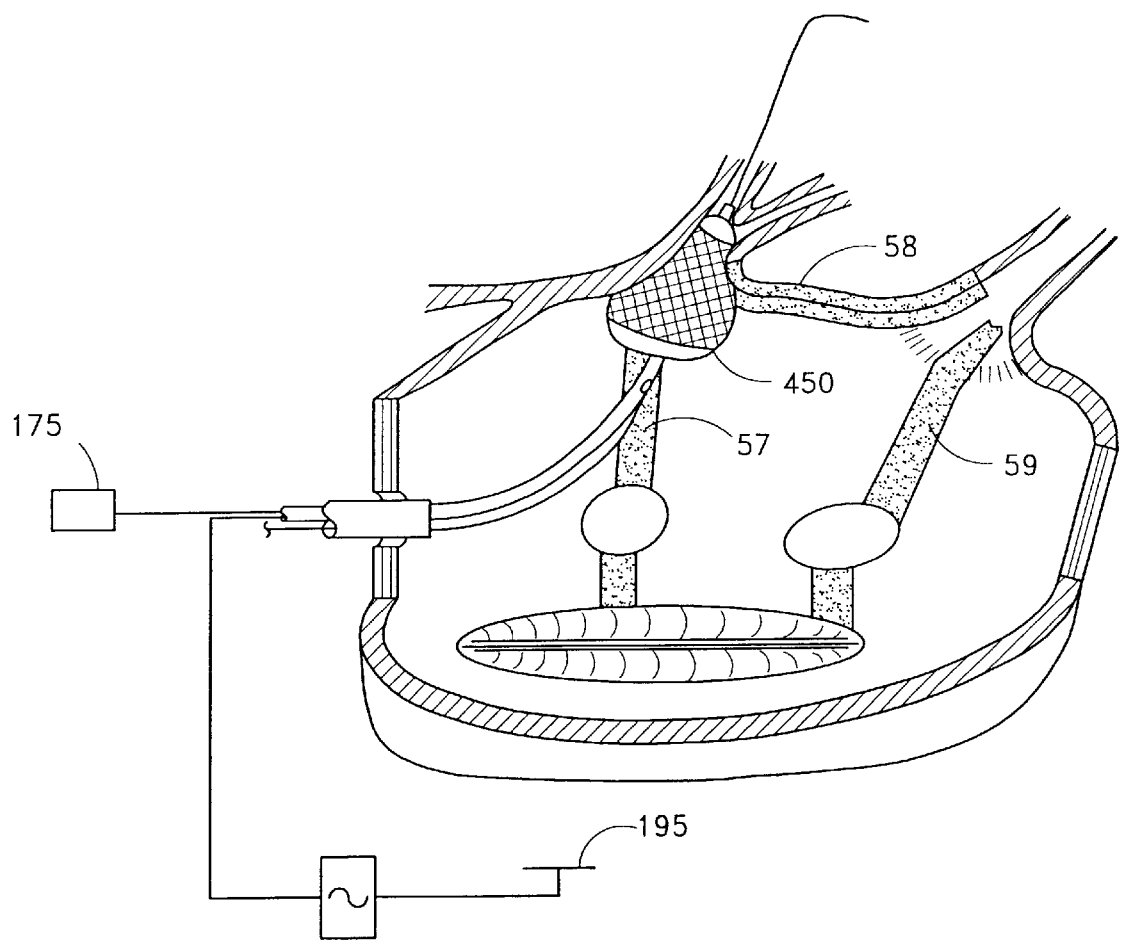
FIG. 8C shows a similar perspective view as that shown in FIG. 8B, although showing a circumferential ablation device assembly during use in forming a circumferential lesion in a pulmonary vein which intersects with two linear lesions that extend into the pulmonary vein, according to the method of FIG. 8A.
Figure 8D:
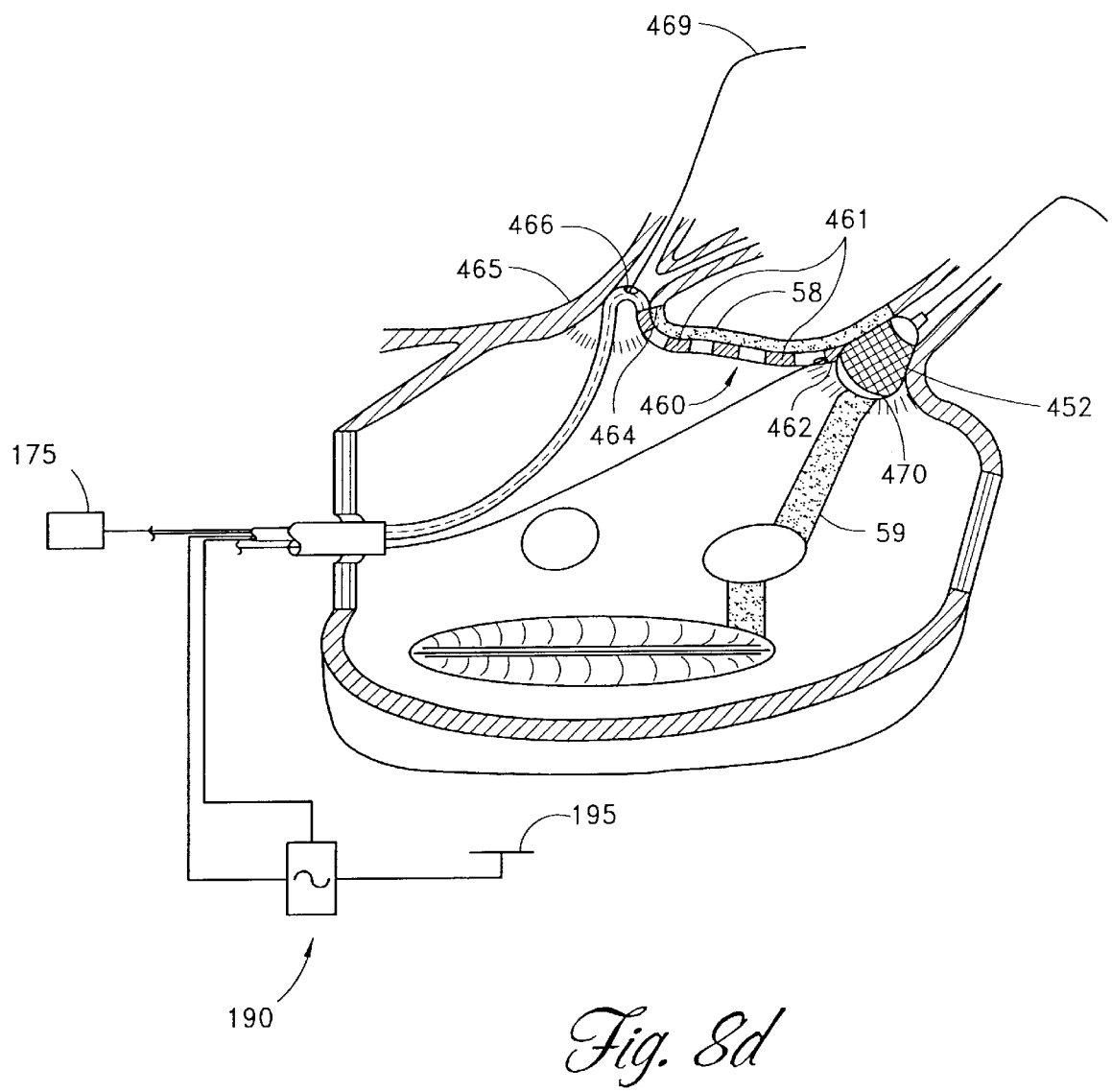
FIG. 8D shows a perspective view of another circumferential ablation catheter during use according to the method of FIG. 8A, wherein a circumferential ablation member is provided on an elongate catheter body adjacent to a linear ablation member such that circumferential and linear lesions formed in pulmonamy vein wall tissue by the two ablation elements, respectively, intersect.

In a further variation to the specific embodiments shown in FIGS. 8B–C, FIG. 8D shows a circumferential ablation device assembly which includes both circumferential and linear ablation elements (452,460), respectively. Circumferential ablation member (450) is shown to include an expandable member (470) which is adjusted to a radially expand position that is asymmetric to the underlying catheter shaft. Linear ablation member (460) extends along the elongate body proximally from the circumferential ablation member (450). When expanded sufficiently to engage the pulmonary vein wall, expandable member (470) provides at least a portion of an anchor for a first end (462) of linear ablation member (460).

A shaped stylet (466) is shown in shadow in FIG. 8D within the elongate catheter body in the region of the second end (464) of the linear ablation member (460). Shaped stylet (466) includes a port or opening (465) though which guidewire (469) passes in order to anchor the second end (464) into an adjacent pulmonary vein ostium such that the linear ablation member (460) is adapted to substantially contact the left atrial wall between the adjacent vein ostia to form the linear ablation according to the method of FIG. 8A. Alternatively to the use of shaped stylet (466) and guidewire (469), it is further contemplated that a second anchor may be effected with, for example, an intermediate guidewire tracking member adapted to track over a guidewire (469) engaged to the pulmonary vein.

Figure 9:
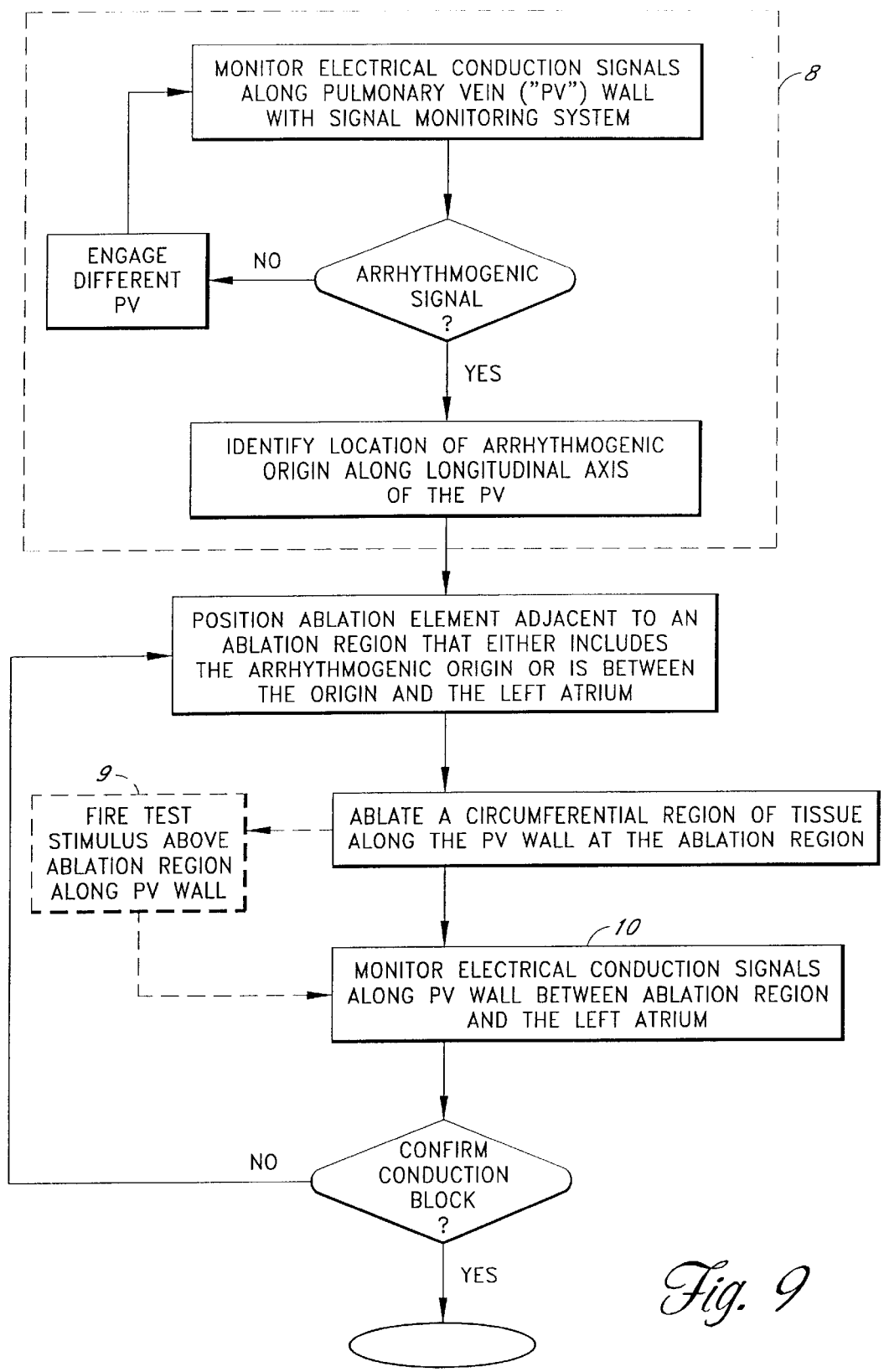
FIG. 9 diagrammatically shows a further method for using the circumferential ablation device assembly of the present invention to form a circumferential conduction block in a pulmonary vein wall, wherein signal monitoring and "post-ablation" test elements are used to locate an arrhythmogenic origin along the pulmonary vein wall and to test the efficacy of a circumferential conduction block in the wall, respectively.

FIG. 9 diagrammatically shows a further method for using the circumferential ablation device assembly of the present invention wherein electrical signals along the pulmonary vein are monitored with a sensing element before and after ablation according to steps (8) and (9), respectively. Signals within the pulmonary vein are monitored prior to forming a conduction block, as indicated in step (8) in FIG. 9, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation, according to step (9) of the method of FIG. 9. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method according to step (10) of FIG. 9. In one particular embodiment not shown, the test electrode is positioned on the distal end portion of an elongate catheter body and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself, as will be further developed below.

Circumferential Ablation Member

The designs for the expandable member and circumferential ablation element for use in the circumferential ablation device assembly of the present invention have been described generically with reference to the embodiments shown in the previous Figures. Examples of more specific expandable member and ablation element embodiments which are adapted for use in the assembly of the present invention are further provided as follows.

Notwithstanding their somewhat schematic detail, the circumferential ablation members shown in the previous figures do illustrate one particular embodiment wherein a circumferential electrode element circumscribes an outer surface of an expandable member. The expandable member of the embodiments shown may take one of several different forms, although the expandable member is generally herein shown as an inflatable balloon that is coupled to an expansion actuator (175) which is a pressurizeable fluid source. The balloon is preferably made of a polymeric material and forms a fluid chamber which communicates with a fluid passageway (not shown in the figures) that extends proximally along the elongate catheter body and terminates proximally in a proximal fluid port that is adapted to couple to the pressurizeable fluid source.

In one expandable balloon variation, the balloon is constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters, with each balloon working length having a unique predetermined expanded diameter, may be provided from which a treating physician may chose a particular device to meet a particular patient's pulmonary vein anatomy.

In an alternative expandable balloon variation, the balloon is constructed of a relatively compliant, elastomeric material, such as, for example (but not limited to), a silicone, latex, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 7A–B. Further to this conformability to pulmonary vein ostium as provided in the specific design of FIGS. 7A–B, the working length L of expandable member (370) is also shown to include a taper which has a distally reducing outer diameter from a proximal end (372) to a distal end (374). In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Further to the circumferential electrode element embodiment as shown variously throughout the previous illustrative Figures, the circumferential electrode element is coupled to an ablation actuator (190). Ablation actuator (190) generally includes a radio-frequency ("RF") current source (not shown) that is coupled to both the RF electrode element and also a ground patch (195) which is in skin contact with the patient to complete an RF circuit. In addition, ablation actuator (190) preferably includes a monitoring circuit (not shown) and a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

FIGS. 10A–D show various patterns of electrically conductive, circumferential electrode bands as electrode ablation elements, each circumscribing an outer surface of the working length of an expandable member. FIGS. 10A–B show circumferential ablation member (550) to include a continuous circumferential electrode band (552) that circumscribes an outer surface of an expandable member (570). FIG. 10B more specifically shows expandable member (570) as a balloon which is fluidly coupled to a pressurizeable fluid source (175), and further shows electrode band (circumferential ablation element) (552) electrically coupled via electrically conductive lead (554) to ablation actuator (190). In addition, a plurality of apertures (572) are shown in the balloon skin wall of expandable member (570) adjacent to electrode band (552). The purpose of these apertures (572) is to provide a positive flow of fluid such as saline or ringers lactate fluid into the tissue surrounding the electrode band (552). Such fluid flow is believed to reduce the temperature rise in the tissue surrounding the electrode element during RF ablation.

The shapes shown collectively in FIGS. 10A–D allow for a continuous electrode band to circumscribe an expandable member's working length over a range of expanded diameters, a feature which is believed to be particularly useful with a relatively compliant balloon as the expandable member. In the particular embodiments of FIGS. 10A–D, this feature is provided primarily by a secondary shape given to the electrode band relative to the longitudinal axis of the working length of the expandable member. Electrode band (552) is thus shown in FIGS. 10A–B to take the specific secondary shape of a modified step curve. Other shapes than a modified step curve are also suitable, such as the serpentine or sawtooth secondary shapes shown respectively in FIGS. 10C–D. Other shapes in addition to those shown in FIGS. 10A–D and which meet the defined functional requirements are further contemplated within the scope of the present invention.

In addition, the electrode band provided by the circumferential ablation elements shown in FIGS. 10C–D and also shown schematically in FIGS. 3–5 has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band which has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement which is believed to be suitable for ablating circumferential lesions in the pulmonary veins as conduction blocks, the band width w is less than 1 cm with a circumference on the working length when expanded that is greater than 1.5 cm.

FIGS. 11A–B show a further variation of a circumferential ablation element which is adapted to maintain a continuous circumferential lesion pattern over a range of expanded diameters and which includes electrode elements that form a relatively narrow equatorial band around the working length of an expandable balloon member. In this variation, a plurality of individual electrode/ablation elements (562) are included in the circumferential ablation element and are positioned in spaced arrangement along an equatorial band which circumscribes an outer surface of the expandable member's working length L.

The size and spacing between these individual electrode elements (562), when the balloon is expanded, is adapted to form a substantially continuous circumferential lesion in pulmonary vein wall tissue when in intimal contact adjacent thereto, and is further adapted to form such a lesion over a range of band diameters as the working length is adjusted between a variety of radially expanded positions. Each individual electrode element (562) has two opposite ends (563,564), respectively, along a long axis LA and also has a short axis SA, and is positioned such that the long axis LA is at an acute angle relative to the longitudinal axis La of the elongate catheter body and expandable member (560). At least one of the ends (563,564) along the long axis LA overlaps with an end of another adjacent individual electrode element, such that there is a region of overlap along their circumferential aspect, i.e., there is a region of overlap along the circumferential coordinates. The terms "region of overlap along their circumferential coordinate" are herein intended to mean that the two adjacent ends each are positioned along the working length with a circumferential and also a longitudinal coordinate, wherein they share a common circumferential coordinate. In this arrangement, the circumferential compliance along the working length which accompanies radial expansion of the expandable member also moves the individual electrode elements apart along the circumferential axis. However, the spaced, overlapping arrangement described allows the individual ablation elements to maintain a certain degree of their circumferential overlap, or at least remain close enough together, such that a continuous lesion may be formed without gaps between the elements.

The construction for suitable circumferential electrode elements in the RF variation of the present invention, such as the various electrode embodiments described with reference to FIGS. 10A–12B, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered within the scope of the present invention, so long as they form a circumferential conduction block as previously described. For example, a balloon skin may itself be metallized, such as by mixing conductive metal, including but not limited to gold, platinum, or silver, with a polymer to form a compounded, conductive matrix as the balloon skin.

Still further to the RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous polymeric material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element which may, for example, be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be, for example, a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40 deg and 80 deg Celsius.

Further to the thermal conduction variation for the circumferential ablation element, the perfusion balloon embodiment as shown in FIGS. 5A–B may be particularly useful in such a design. It is believed that ablation through increased temperatures, as provided by example above may also enhance coagulation of blood in the pulmonay vein adjacent to the expandable member, which blood would otherwise remain stagnant without such a perfusion feature.

One further circumferential ablation element design which is believed to be highly useful in performing the methods according to the present invention is shown in FIG. 12 to include a circumferential ablation member (600) with two insulators (602,604) that encapsulate the proximal and distal ends, respectively, of the working length L of an expandable member (610). In the particular embodiment shown, the insulators (602,604) are thermal insulators, such as a thermal insulator comprising a Teflon material. Expandable member (610) is an inflatable balloon which has a balloon skin (612) that is thermally conductive to surrounding tissue when inflated with a heated fluid which may contain a radiopaque agent, saline fluid, ringers lactate, combinations thereof, other known biocompatible fluids having acceptable heat transfer properties for these purposes, further to the thermal conductor embodiments previously described. By providing these spaced insulators, a circumferential ablation element is formed as an equatorial band (603) of uninsulated balloon skin is located between the opposite insulators. In this configuration, the circumferential ablation element is able to conduct heat externally of the balloon skin much more efficiently at the uninsulated equatorial band (603) than at the insulated portions, and thereby is adapted to ablate only a circumferential region of tissue in a pulmonary vein wall which is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 12 further shows use of a radiopaque marker (620) to identify the location of the equatorial band (603) in order to facilitate placement of that band at a selected ablation region of a pulmonary vein via X-ray visualization. Radiopaque marker (620) is opaque under X-ray, and may be constructed, for example, of a radiopaque metal such as gold, platinum, or tungsten, or may comprise a radiopaque polymer such as a metal loaded polymer. FIG. 12 shows radiopaque marker (620) positioned coaxially over an inner tubular member (621) which is included in a coaxial catheter design as would be apparent to one of ordinary skill. The present invention contemplates the combination of such a radiopaque marker additionally in the other embodiments herein shown and described. To note, when the circumferential ablation member which forms an equatorial band includes a metallic electrode element, such electrode may itself be radiopaque and may not require use of a separate marker as just described.

The thermal insulator embodiment just described by reference to FIG. 12 is illustrative of a broader embodiment, wherein a circumferential ablation member has an ablating surface along the entire working length of an expandable member, but is shielded from releasing ablative energy into surrounding tissues except for along an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon which includes a conductive balloon skin may have an electrical insulator, such as a polymeric coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

In still a further example of an insulator combined with an RF ablation electrode, a porous membrane comprises the entire balloon skin of an expandable member. By insulating the proximal and distal end portions of the working length of the expandable member, only the pores in the unexposed equatorial band region are allowed to effuse the electrolyte which carries an ablative RF current.

Further to the expandable member design for use in a circumferential ablation element according to the present invention, other expandable members than a balloon are also considered suitable. For example, in one expandable cage embodiment shown in FIG. 13, cage (650) comprises coordinating wires (651) and is expandable to engage a desired ablation region in a pulmonary vein.

The radial expansion of cage (650) is accomplished as follows. Sheath (652) is secured around the wires proximally of cage (650). However, core (653), which may be a metallic mandrel such as stainless steel, extends through sheath (652) and distally within cage (650) wherein it terminates in a distal tip (656). Wires (651) are secured to distal tip (656), for example, by soldering, welding, adhesive bonding, heat shrinking a polymeric member over the wires, or any combination of these methods. Core (653) is slideable within sheath (652), and may, for example, be housed within a tubular lumen (not shown) within sheath (652), the wires being housed between a coaxial space between the tubular lumen and sheath (652). By moving the sheath (652) relative to core (653) and distal tip (656)(shown by arrows in FIG. 13), the cage (650) is collapsible along its longitudinal axis in order to force an outward radial bias (also shown with arrows in FIG. 13) to wires (651) in an organized fashion to formed a working length of cage (650) which is expanded (not shown).

Further to the particular expandable cage embodiment shown in FIG. 13, a plurality of ablation electrodes (655) is shown, each being positioned on one of wires (651) and being similarly located along the longitudinal axis of the cage (650). The radial bias given to wires (651) during expansion, together with the location of the ablation electrodes (655), serves to position the plurality of ablation electrodes/elements (655) along a circumferential, equatorial band along the expanded working length of cage (650). The wires forming a cage according to this embodiment may also have another predetermined shape when in the radially expanded position. For example, a taper similar to that shown for expandable member (370) in FIGS. 7A–B may be formed by expanding cage (650), wherein the ablation element formed by ablation electrodes (655) may be positioned between the proximal end and the distal end of the taper.

Further to the construction of the embodiment shown in FIG. 13, wires (651) are preferably metal, and may comprise stainless steel or a superelastic metal alloy, such as an alloy of nickel and titanium, or a combination of both. Regarding the case of nickel and titanium construction for wires (655), a separate electrical conductor may be required in order to actuate ablation electrodes (655) to efficiently emit ablative current into surrounding tissues. In the case where wires (651) are constructed of stainless steel, they may also serve as electrical conductors for ablation electrodes (655). Further to the stainless steel design, the wires (651) may be coated with an electrical insulator to isolate the electrical flow into surrounding tissues at the site of the ablation electrodes (655). Moreover, the ablation electrodes (655) in the stainless steel wire variation may be formed simply by removing electrical insulation in an isolated region to allow for current to flow into tissue only from that exposed region.

In a further cage embodiment (not shown) to that shown in FIG. 13, a circumferential strip of electrodes may also be secured to the cage (650) such that the strip circumscribes the cage at a predetermined location along the cage's longitudinal axis. By expanding cage (650) as previously described, the strip of electrodes are adapted to take a circumferential shape according to the shape of the expanded cage (650). Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip which includes several separate electrodes along its circumferential length. In the latter case, the flexible strip may electrically couple all of the electrodes to a conductive lead that interfaces with a drive circuit, or each electrode may be separately coupled to one or more such conductive leads.

Figure 14:
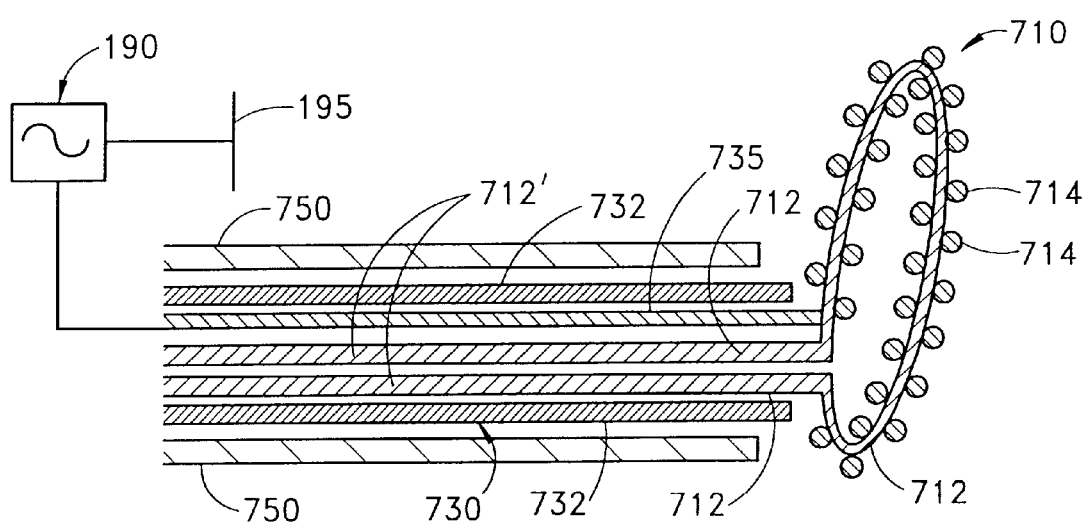
FIG. 14 shows a cross-sectional view of another circumferential ablation element which is adapted for use in the circumferential ablation device assembly of the present invention. A superelastic, looped electrode element is shown at the distal end of a pusher and is adapted to circumferentially engage pulmonary vein wall tissue to form a circumferential lesion as a conduction block that circumscribes the pulmonary vein lumen.

Another circumferential ablation element adapted for use in the circumferential conduction block assembly according to the present invention is shown in FIG. 14, wherein circumferential ablation member (700) includes a looped member (710) attached, preferably by heat shrinking, to a distal end of a pusher (730). Looped member (710) and pusher (730) are slideably engaged within delivery sheath (750) such that looped member (710) is in a first collapsed position when positioned and radially confined within delivery sheath (750), and expands to a second expanded position when advanced distally from delivery sheath (750).

Looped member (710) is shown in more detail in FIG. 14 to include a core (712) which is constructed of a superelastic metal alloy such as a nickel-titanium alloy and which has a looped portion with shape memory in the looped configuration. This looped configuration is shown in FIG. 14 to be in a plane which is off-axis, preferably perpendicular, to the longitudinal axis of the pusher (730). This off-axis orientation of the loop is adapted to engage a circumferential path of tissue along a pulmonary vein wall which circumscribes the pulmonary vein lumen when the looped member (710) is delivered from the delivery sheath (750) when the delivery sheath is positioned within the vein lumen parallel to its longitudinal axis. An ablation electrode (714) is also shown in FIG. 14 as a metallic coil which is wrapped around core (712) in its looped portion.

Pusher (730) is further shown in FIG. 14 to include a tubular pusher member (732) which is heat shrunk over two ends (712') of core (712) which extend proximally of looped member (710) through pusher (730) in the particular variation shown. While in this embodiment core (712) extends through the pusher in order to provide stiffness to the composite design for the pusher, it is further contemplated that the superelastic metal of the core may be replaced or augmented in the pusher region with another different mandrel or pusher core (not shown), such as a stiffer stainless steel mandrel. Also shown within pusher (730) is an electrically conductive lead (735) which is coupled to the ablation electrode (714) and which is also adapted in a proximal region of the pusher (not shown) to couple to an ablation actuator (190) such as an RF current source (shown schematically).

Ultrasound Circumferential Ablation Member

FIGS. 15A–18B show various specific embodiments of a broader circumferential ablation device assembly which utilizes an ultrasonic energy source to ablate tissue. The present circumferential ablation device has particular utility in connection with forming a circumferential lesion within or about a pulmonary vein ostium or within the vein itself in order to form a circumferential conductive block. This application of the present ablation device, however, is merely exemplary, and it is understood that those skilled in the art can readily adapt the present ablation device for applications in other body spaces.

As common to each of the following embodiments, a source of acoustic energy is provided a delivery device that also includes an anchoring mechanism. In one mode, the anchoring device comprises an expandable member that also positions the acoustic energy source within the body; however, other anchoring and positioning devices may also be used, such as, for example, a baket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of 1 millimeter to 10 millimeters. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIGS. 15A through 15D, a circumferential ablation device assembly (800) includes an elongate body (802) with proximal and distal end portions (810,812), an expandable balloon (820) located along the distal end portion (812) of elongate body (802), and a circumferential ultrasound transducer (830) which forms a circumferential ablation member which is acoustically coupled to the expandable balloon (820). In more detail, FIGS. 15A–C variously show elongate body (802) to include guidewire lumen (804), inflation lumen (806), and electrical lead lumen (808). The ablation device, however, can be of a self steering type rather than an over-the-wire type device.

Each lumen extends between a proximal port (not shown) and a respective distal port, which distal ports are shown as distal guidewire port (805) for guidewire lumen (804), distal inflation port (807) for inflation lumen (806), and distal lead port (809) for electrical lead lumen (808). Although the guidewire, inflation and electrical lead lumens are generally arranged in a side-by-side relationship, the elongate body (802) can be constructed with one or more of these lumens arranged in a coaxial relationship, or in any of a wide variety of configurations that will be readily apparent to one of ordinary skill in the art.

In addition, the elongate body (802) is also shown in FIGS. 15A and 15C to include an inner member (803) which extends distally beyond distal inflation and lead ports (807, 809), through an interior chamber formed by the expandable balloon (820), and distally beyond expandable balloon (820) where the elongate body terminates in a distal tip. The inner member (803) forms the distal region for the guidewire lumen (804) beyond the inflation and lead ports, and also provides a support member for the cylindrical ultrasound transducer (830) and for the distal neck of the expansion balloon, as described in more detail below.

One more detailed construction for the components of the elongate body (802) which is believed to be suitable for use in transeptal left atrial ablation procedures is as follows. The elongate body (802) itself may have an outer diameter provided within the range of from about 5 French to about 10 French, and more preferable from about 7 French to about 9 French. The guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although may vary based upon the viscosity of inflation medium used, length of the lumen, and other dynamic factors relating to fluid flow and pressure.

In addition to providing the requisite lumens and support members for the ultrasound transducer assembly, the elongate body (802) of the present embodiment must also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion (812) is preferably flexible and adapted to track over and along a guidewire seated within the targeted pulmonary vein. In one further more detailed construction which is believed to be suitable, the proximal end portion is adapted to be at least 30% more stiff than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the ultrasound ablation member to the desired ablation region are also contemplated. For example, while the FIG. 15A variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter.

In another example, a deflectable tip design may also be a suitable substitute and which is adapted to independently select a desired pulmonary vein and direct the transducer assembly into the desired location for ablation. Further to this latter variation, the guidewire lumen and guidewire of the FIG. 15A variation may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

More specifically regarding expandable balloon (820) as shown in varied detail between FIGS. 15A and 15C, a central region (822) is generally coaxially disposed over the inner member (803) and is bordered at its end neck regions by proximal and distal adaptions (824,826). The proximal adaption (824) is sealed over elongate body (802) proximally of the distal inflation and the electrical lead ports (807,809), and the distal adaption (826) is sealed over inner member (803). According to this arrangement, a fluid tight interior chamber is formed within expandable balloon (820). This interior chamber is fluidly coupled to a pressurizeable fluid source (not shown) via inflation lumen (806). In addition to the inflation lumen (806), electrical lead lumen (808) also communicates with the interior chamber of expandable balloon (820) so that the ultrasound transducer (830), which is positioned within that chamber and over the inner member (803), may be electrically coupled to an ultrasound drive source or actuator, as will be provided in more detail below.

The expandable balloon (820) may be constructed from a variety of known materials, although the balloon (820) preferably is adapted to conform to the contour of a pulmonary vein ostium. For this purpose, the balloon material can be of the highly compliant variety, such that the material elongates upon application of pressure and takes on the shape of the body lumen or space when fully inflated. suitable balloon materials include elastomers, such as, for example, but without limitation, Silicone, latex, or low durometer polyurethane (for example, a durometer of about 80A).

In addition or in the alternative to constructing the balloon of highly compliant material, the balloon (820) can be formed to have a predefined fully inflated shape (i.e., be preshaped) to generally match the anatomic shape of the body lumen in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon (820) is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to change in diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion ratio).

The ablation member, which is illustrated in FIGS. 15A–D, takes the form of annular ultrasonic transducer (830). In the illustrated embodiment, the annular ultrasonic transducer (830) has a unitary cylindrical shape with a hollow interior (i.e., is tubular shaped); however, the transducer applicator (830) can have a generally annular shape and be formed of a plurality of segments. For instance, the transducer applicator (830) can be formed by a plurality of tube sectors that together form an annular shape. The tube sectors can also be of sufficient arc lengths so as when joined together, the sectors assembly forms a "clover-leaf" shape. This shape is believed to provide overlap in heated regions between adjacent elements. The generally annular shape can also be formed by a plurality of planar transducer segments which are arranged in a polygon shape (e.g., hexagon). In addition, although in the illustrated embodiment the ultrasonic transducer comprises a single transducer element, the transducer applicator can be formed of a multi-element array, as described in greater detail below.

As is shown in detail in FIG. 15D, cylindrical ultrasound transducer (830) includes a tubular wall (831) which includes three concentric tubular layers. The central layer (832) is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members (833,834) enclose central layer (832) within their coaxial space and are constructed of an electrically conductive material. In the illustrated embodiment, these transducer electrodes (833, 834) comprise a metallic coating, and more preferably a coating of nickel, copper, silver, gold, platinum, or alloys of these metals.

One more detailed construction for a cylindrical ultrasound transducer for use in the present application is as follows. The length of the transducer (830) or transducer assembly (e.g., multi-element array of transducer elements) desirably is selected for a given clinical application. In connection with forming circumferential condition blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer (830) preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer applicator (830) may have an outer diameter within the range of about 1 mm to greater than 3–4 mm (e.g., as large as 1 to 2 cm for applications in some body spaces).

The central layer (832) of the transducer (830) has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer (830) in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer (830) is vibrated across the wall thickness and to radiate collimated acoustic energy in the radial direction. For this purpose, as best seen in FIGS. 15A and 15D, the distal ends of electrical leads (836,837) are electrically coupled to outer and inner tubular members or electrodes (833,834), respectively, of the transducer (830), such as, for example, by soldering the leads to the metallic coatings or by resistance welding. In the illustrated embodiment, the electrical leads are 4–8 mil (0.004 to 0.008 inch diameter) silver wire or the like.

The proximal ends of these leads are adapted to couple to an ultrasonic driver or actuator (840), which is schematically illustrated in FIG. 15D. FIGS. 15A–D further show leads (836,837) as separate wires within electrical lead lumen (808), in which configuration the leads must be well insulated when in close contact. Other configurations for leads (836,837) are therefore contemplated. For example, a coaxial cable may provide one cable for both leads which is well insulated as to inductance interference. Or, the leads may be communicated toward the distal end portion (812) of the elongate body through different lumens which are separated by the catheter body.

The transducer also can be sectored by scoring or notching the outer transducer electrode (833) and part of the central layer (832) along lines parallel to the longitudinal axis L of the transducer (830), as illustrated in FIG. 15E. A separate electrical lead connects to each sector in order to couple the sector to a dedicated power control that individually excites the corresponding transducer sector. By controlling the driving power and operating frequency to each individual sector, the ultrasonic driver (840) can enhance the uniformity of the ultrasonic beam around the transducer (830), as well as can vary the degree of heating (i.e., lesion control) in the angular dimension.

The ultrasound transducer just described is combined with the overall device assembly according to the present embodiment as follows. In assembly, the transducer (830) desirably is "air-backed" to produce more energy and to enhance energy distribution uniformity, as known in the art. In other words, the inner member (803) does not contact an appreciable amount of the inner surface of transducer inner tubular member (834). This is because the piezoelectric crystal which forms central layer (832) of ultrasound transducer (830) is adapted to radially contract and expand (or radially "vibrate") when an alternating current is applied from a current source and across the outer and inner tubular electrodes (833,834) of the crystal via the electrical leads (836,837). This controlled vibration emits the ultrasonic energy which is adapted to ablate tissue and form a circumferential conduction block according to the present embodiment. Therefore, it is believed that appreciable levels of contact along the surface of the crystal may provide a dampening effect which would diminish the vibration of the crystal and thus limit the efficiency of ultrasound transmission.

For this purpose, the transducer (830) seats coaxial about the inner member (803) and is supported about the inner member (803) in a manner providing a gap between the inner member (803) and the transducer inner tubular member (834). That is, the inner tubular member (834) forms an interior bore (835) which loosely receives the inner member (803). Any of a variety of structures can be used to support the transducer (830) about the inner member (803). For instance, spaces or splines can be used to coaxially position the transducer (830) about the inner member (803) while leaving a generally annular space between these components. In the alternative, other conventional and known approaches to support the transducer can also be used. For instance, O-rings that circumscribe the inner member (803) and lie between the inner member (803) and the transducer (830) can support the transducer (830) in a manner similar to that illustrated in U.S. Pat. No. 5,606,974, issued Mar. 4, 1997, and entitled "Catheter Having Ultrasonic Device." More detailed examples of the alternative transducer support structures just described are respectfully disclosed in the following references: U.S. Pat. No. 5,620,479 to Diederich, issued Apr. 15, 1997, and entitled "Method and Apparatus for Thermal Therapy of Tumors," and U.S. Pat. No. 5,606,974 to Castellano, issued Mar. 4, 1997, and entitled "Catheter Having Ultrasonic Device." The disclosures of these references are herein incorporated in their entirety by reference thereto.

In the illustrated embodiment, a stand-off (838) is provided in order to ensure that the transducer (830) has a radial separation from the inner member (803) to form a gap filled with air and/or other fluid. In one preferred mode shown in FIG. 15D, stand-off (838) is a tubular member with a plurality of circumferentially spaced outer splines (839) which hold the majority of the transducer inner surface away from the surface of the stand-off between the splines, thereby minimizing dampening affects from the coupling of the transducer to the catheter. The tubular member which forms a stand-off such as stand-off (838) in the FIG. 15D embodiment may also provide its inner bore as the guidewire lumen in the region of the ultrasound transducer, in the alternative to providing a separate stand-off coaxially over another tubular member which forms the inner member, such as according to the FIG. 15D embodiment.

In a further mode, the elongate body (802) can also include additional lumens which lie either side by side to or coaxial with the guidewire lumen (804) and which terminate at ports located within the space between the inner member (803) and the transducer (830). A cooling medium can circulate through space defined by the stand-off (838) between the inner member (803) and the transducer (830) via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer (830) desirably is electrically and mechanically isolated from the interior of the balloon (820). Again, any of a variety of coatings, sheaths, sealants, tubings and the like may be suitable for this purpose, such as those described in U.S. Pat. Nos. 5,620,479 and 5,606,974. In the illustrated embodiment, as best illustrated in FIG. 15C, a conventional, flexible, acoustically compatible, and medical grade epoxy (842) is applied over the transducer (830). The epoxy (842) may be, for example, Epotek 301, Epotek 310, which is available commercially from Epoxy Technology, or Tracon FDA-8. In addition, a conventional sealant, such as, for example, General Electric Silicon II gasket glue and sealant, desirably is applied at the proximal and distal ends of the transducer (830) around the exposed portions of the inner member (803), wires (836, 837) and stand-off (838) to seal the space between the transducer (830) and the inner member (803) at these locations.

An ultra thin-walled polyester heat shrink tubing (844) or the like then seals the epoxy coated transducer. Alternatively, the epoxy covered transducer (830), inner member (803) and stand-off (838) can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer (830). As the tube shrinks, excess epoxy flows out and a thin layer of epoxy remains between the transducer and the heat shrink tubing (844). These layers (842, 844) protect the transducer surface, help acoustically match the transducer (830) to the load, makes the ablation device more robust, and ensures air-tight integrity of the air backing.

Although not illustrated in FIG. 15A in order to simplify the drawing, the tubing (844) extends beyond the ends of transducer (830) and surrounds a portion of the inner member (803) on either side of the transducer (830). A filler (not shown) can also be used to support the ends of the tubing (844). Suitable fillers include flexible materials such as, for example, but without limitation, epoxy, Teflon® tape and the like.

The ultrasonic actuator (840) generates alternating current to power the transducer (830). The ultrasonic actuator (840) drives the transducer (830) at frequencies within the range of about 5 to about 20 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator (840) can drive the transducer at frequencies within the range of 6.8 MHz and 7.2 MHz by continuously or discretely sweeping between these frequencies.

The ultrasound transducer (830) of the present embodiment sonically couples with the outer skin of the balloon (820) in a manner which forms a circumferential conduction block in a pulmonary vein as follows. Initially, the ultrasound transducer is believed to emit its energy in a circumferential pattern which is highly collimated along the transducer's length relative to its longitudinal axis L (see FIG. 15D). The circumferential band therefore maintains its width and circumferential pattern over an appreciable range of diameters away from the source at the transducer. Also, the balloon is preferably inflated with fluid which is relatively ultrasonically transparent, such as, for example, degassed water. Therefore, by actuating the transducer (830) while the balloon (820) is inflated, the circumferential band of energy is allowed to translate through the inflation fluid and ultimately sonically couple with a circumferential band of balloon skin which circumscribes the balloon (820). Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

Figure 16A:
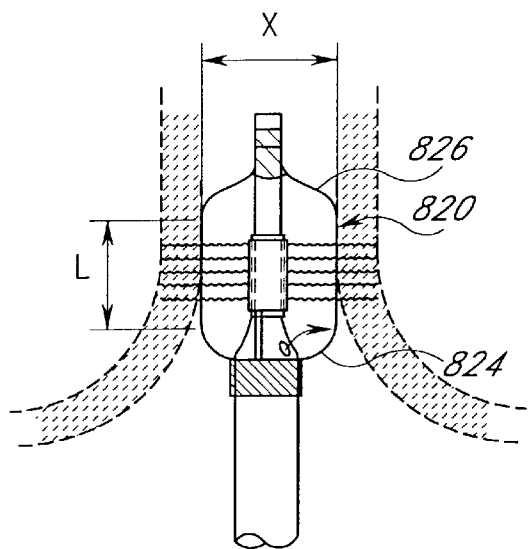
FIG. 16A shows a perspective view of a similar circumferential ablation catheter to the catheter shown in FIG. 15, and shows the distal end portion of the circumferential ablation catheter during one mode of use in forming a circumferential conduction block in a pulmonary vein in the region of its ostium along a left atrial wall (shown in cross-section in shadow).

In one particular balloon-transducer combination shown in FIG. 15C and also in FIG. 16A, the ultrasound transducer preferably has a length such that the ultrasonically coupled band of the balloon skin, having a similar length d according to the collimated electrical signal, is shorter than the working length D of the balloon. According to this aspect of the relationship, the transducer is adapted as a circumferential ablation member which is coupled to the balloon to form an ablation element along a circumferential band of the balloon, therefore forming a circumferential ablation element band which circumscribes the balloon. Preferably, the transducer has a length which is less than two-thirds the working length of the balloon, and more preferably is less than one-half the working length of the balloon. By sizing the ultrasonic transducer length d smaller than the working length D of the balloon (820)—and hence shorter than a longitudinal length of the engagement area between the balloon (820) and the wall of the body space (e.g., pulmonary vein ostium)—and by generally centering the transducer (830) within the balloon's working length D, the transducer (830) operates in a field isolated from the blood pool. A generally equatorial position of the transducer (830) relative to the ends of the balloon's working length also assists in the isolation of the transducer (830) from the blood pool.

It is believed that the transducer placement according to this arrangement may be preventative of thrombus formation which might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate body (802) may include an additional radiopaque marker or markers (not shown) to identify the location of the ultrasonic transducer (830) in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The radiopaque marker is positioned coaxially over an inner tubular member (803), in a manner similar to that described in connection with the embodiment of FIG. 12.

The present circumferential ablation device is introduced into a pulmonary vein of the left atrium in a manner similar to that described above. Once properly positioned within the pulmonary vein or vein ostium, the pressurized fluid source inflates the balloon (820) to engage the lumenal surface of the pulmonary vein ostium. Once properly positioned, the ultrasonic driver (840) is energized to drive the transducer (830). It is believed that by driving the ultrasonic transducer 830 at 20 acoustical watts at an operating frequency of 7 megahertz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

Figure 16B:
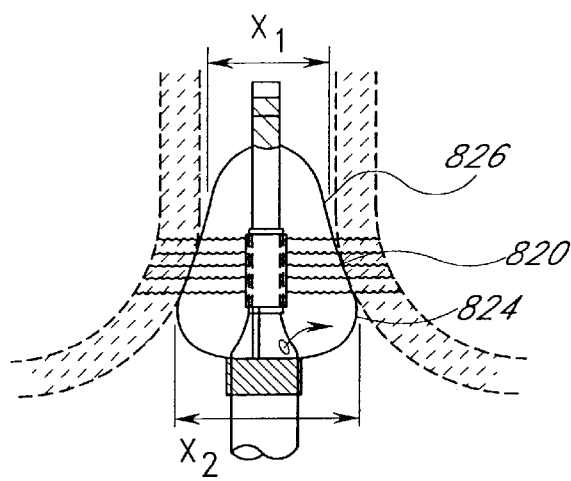
FIG. 16B shows a similar perspective and cross-section shadow view of a circumferential ablation catheter and pulmonary vein ostium as that shown in FIG. 16A, although shows another circumferential ablation catheter wherein the balloon has a tapered outer diameter.
Figure 16C:
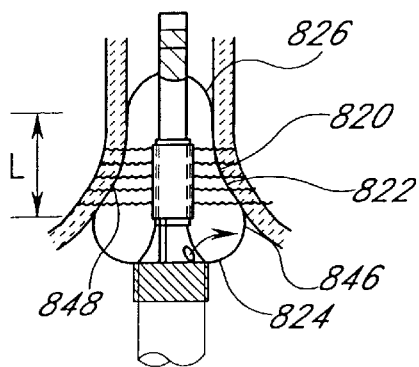
FIG. 16C shows a similar view to that shown in FIGS. 16A–B, although showing another circumferential ablation catheter wherein the balloon has a "pear"-shaped outer diameter with a contoured surface along a taper which is adapted to seat in the ostium of a pulmonary vein.
Figure 16D:
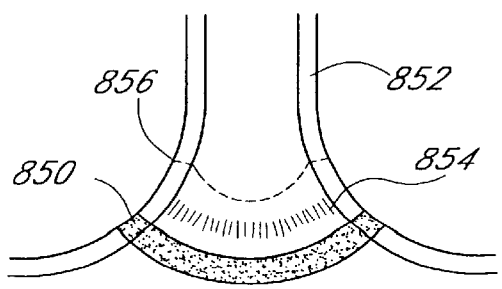
FIG. 16D shows a cross-sectional view of one circumferential conduction block which may be formed by use of a circumferential ablation catheter such as that shown in FIG. 16C.

FIGS. 16A–C show various alternative embodiments of the present invention for the purpose of illustrating the relationship between the ultrasound transducer and balloon of the present invention just described above. More specifically, FIG. 16A shows the balloon (820) having "straight" configuration with a working length D and a relatively constant diameter X between proximal and distal tapers (824, 826). As is shown in FIG. 16A, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon (820).

The balloon (820) in FIG. 16A is also concentrically positioned relative to the longitudinal axis of the elongate body (802). It is understood, however, that the balloon can be asymmetrically positioned on the elongate body, and that the ablation device can include more than one balloon.

FIG. 16B shows another assembly according to the invention, although this assembly includes a balloon (820) which has a tapered outer diameter from a proximal outer diameter $X_1$ to a smaller distal outer diameter $X_2$. (Like reference numerals have been used in each of these embodiments in order to identify generally common elements between the embodiments.) According to this mode, this tapered shape is believed to conform well to other tapering regions of space, and may also be particularly beneficial for use in engaging and ablating circumferential paths of tissue along a pulmonary vein ostium.

FIG. 16C further shows a similar shape for the balloon as that just illustrated by reference to FIG. 16B, except that the FIG. 16C embodiment further includes a balloon (820) and includes a bulbous proximal end (846). In the illustrated embodiment, the proximate bulbous end (846) of the central region (822) gives the balloon (820) a "pear"-shape. More specifically, a contoured surface (848) is positioned along the tapered working length L and between proximal shoulder (824) and the smaller distal shoulder (826) of balloon (820). As is suggested by view of FIG. 16C, this pear shaped embodiment is believed to be beneficial for forming the circumferential conduction block along a circumferential path of atrial wall tissue which surrounds and perhaps includes the pulmonary vein ostium. For example, the device shown in FIG. 16C is believed to be suited to form a similar lesion to that shown at circumferential lesion (850) in FIG. 16D. Circumferential lesion (850) electrically isolates the respective pulmonary vein (852) from a substantial portion of the left atrial wall. The device shown in FIG. 16C is also believed to be suited to form an elongate lesion which extends along a substantial portion of the pulmonary vein ostium (854), e.g., between the proximal edge of the illustrated lesion (850) and the dashed line (856) which schematically marks a distal edge of such an exemplary elongate lesion (850).

As mentioned above, the transducer (830) can be formed of an array of multiple transducer elements that are arranged in series and coaxial. The transducer can also be formed to have a plurality of longitudinal sectors. These modes of the transducer have particular utility in connection with the tapering balloon designs illustrated in FIGS. 16B and 16C. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer (830) is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device (800) can also include additional mechanisms to control the depth of heating. For instance, the elongate body (802) can include an additional lumen which is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon (820) can thus act as a heat sink to conduct away some of the heat from the targeted tissue and maintain the tissue below a desired temperature (e.g., 90 decrees C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer (830) may be mounted on a torquible member which is movably engaged within a lumen that is formed by the elongate body (802).

Another aspect of the balloon-transducer relationship of the present embodiment is also illustrated by reference to FIGS. 17A–B. In general as to the variations embodied by those figures, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 16A–C).

Figure 17A:
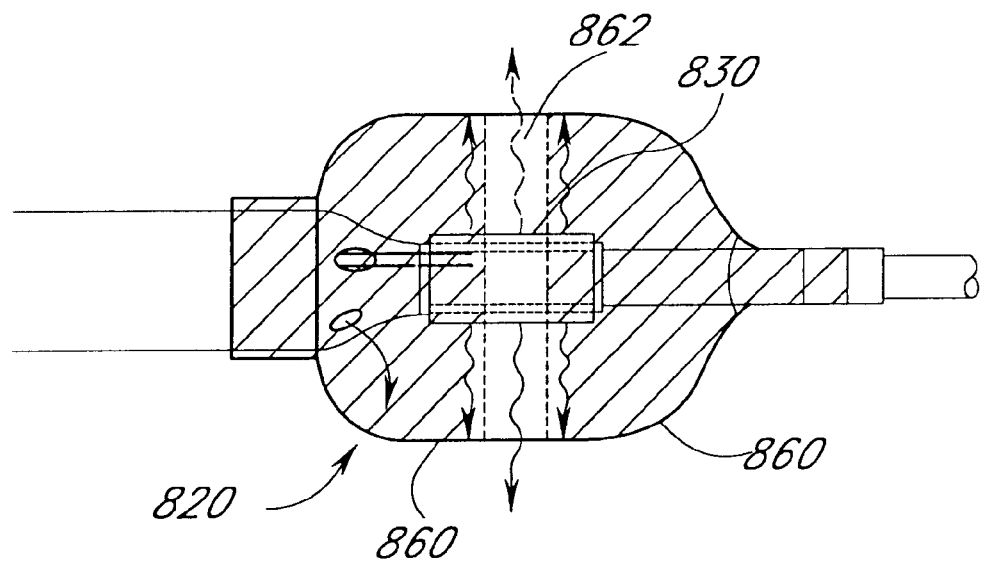
FIG. 17A shows a cross-sectional view of the distal end portion of another circumferential ablation catheter according to the present invention, wherein an outer shield or filter is provided along the balloon's outer surface in order to form a predetermined shape for the circumferential ablation element created by sonic transmissions from the inner ultrasound transducer.

More particularly, FIG. 17A shows balloon (820) to include a filter (860) which has a predetermined pattern along the balloon surface and which is adapted to shield tissue from the ultrasound signal, for example, by either absorbing or reflecting the ultrasound signal. In the particular variation shown in FIG. 17A, the filter (860) is patterned so that the energy band which is passed through the balloon wall is substantially more narrow than the band which emits from the transducer (830) internally of the balloon (820). The filter (860) can be constructed, for example, by coating the balloon (820) with an ultrasonically reflective material, such as with a metal, or with an ultrasonically absorbent material, such as with a polyurathane elastomer. Or, the filter (860) can be formed by varying the balloon's wall thickness such that a circumferential band (862), which is narrow in the longitudinal direction as compared to the length of the balloon, is also thinner (in a radial direction) than the surrounding regions, thereby preferentially allowing signals to pass through the band (862). The thicker walls of the balloon (820) on either side of the band (862) inhibit propagation of the ultrasonic energy through the balloon skin at these locations.

For various reasons, the "narrow pass filter" embodiment of FIG. 17A may be particularly well suited for use in forming circumferential conduction blocks in left atrial wall and pulmonary vein tissues according to the present invention. It is believed that the efficiency of ultrasound transmission from a piezoelectric transducer is limited by the length of the transducer, which limitations are further believed to be a function of the wavelength of the emitted signal. Thus, for some applications a transducer (830) may be required to be longer than the length which is desired for the lesion to be formed. Many procedures intending to form conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length which is much longer and may create lesions which are much wider than is functionally required for the block. A "narrow pass" filter along the balloon provides one solution to such competing interests.

Figure 17B:
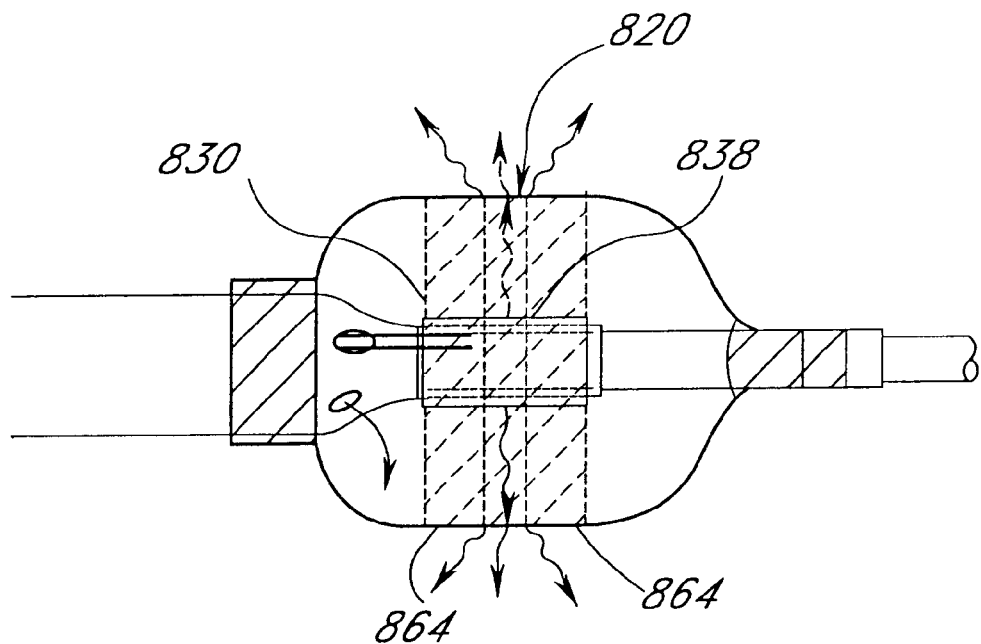
FIG. 17B shows a similar view as that shown in FIG. 17A, although showing the distal end portion of another circumferential ablation catheter which includes a heat sink as an equatorial band within the circumferential path of energy emission from an inner ultrasound transducer.

FIG. 17B shows another variation of the balloon-transducer relationship in an ultrasound ablation assembly according to the present invention. Unlike the variation shown in FIG. 17A, FIG. 17B shows placement of an ultrasonically absorbent band (864) along balloon (820) and directly in the central region of the emitted energy signal from transducer (830). According to this variation, the ultrasonically absorbent band (864) is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, ultrasonically absorbent band (864) may operate as an energy sink as an aid to control the extent of ablation to a less traumatic and invasive level than would be reached by allowing the raw ultrasound energy to couple directly to the tissue. In other words, by heating the absorbent band (864) the signal is diminished to a level that might have a more controlled depth of tissue ablation. Further to this aspect; absorbent band (864) may therefore also have a width which is more commensurate with the length of the transducer, as is shown in an alternative mode in shadow at absorbent band (864).

In each of the embodiments illustrated in FIGS. 15A through 17B, the ultrasonic transducer had an annular shape so as to emit ultrasonic energy around the entire circumference of the balloon. The present circumferential ablation device, however, can emit a collimated beam of ultrasonic energy in a specific angular exposure. For instance, as seen in FIG. 18A, the transducer can be configured to have only a single active sector (e.g., 180 degree exposure). The transducer can also have a planar shape. By rotating the elongate body (802), the transducer (830) can be swept through 360 degrees in order to form a circumferential ablation. For this purpose, the transducer (830) may be mounted on a torquible member (803), in the manner described above.

FIG. 18B illustrates another type of ultrasonic transducer which can be mounted to a torquible member (803) within the balloon (820). The transducer (830) is formed by curvilinear section and is mounted on the inner member (803) with its concave surface facing in a radially outward direction. The inner member (803) desirably is formed with recess that substantially matches a portion of the concave surface of the transducer (830). The inner member (803) also includes longitudinal ridges on the edges of the recess that support the transducer above the inner member such that an air gap is formed between the transducer and the inner member. In this manner, the transducer is "air-backed." This spaced is sealed and closed in the manner described above in connection with the embodiment of FIGS. 15A–E.

The inverted transducer section produces a highly directional beam pattern. By sweeping the transducer through 360 degrees of rotation, as described above, a circumferential lesion can be formed while using less power than would be required with a planar or tubular transducer.

It is to be further understood that the various modes of the ultrasound-balloon embodiments just illustrated by reference to FIGS. 15A–17B may be used according to several different particular methods such as those methods otherwise set forth throughout this disclosure. For example, any of the ultrasound transducer embodiments may be used to form a conduction block in order to prevent or treat focal arrhythmia arising from a specific pulmonary vein, or may alternatively or additionally be used for joining adjacent linear lesions in a less-invasive "maze"-type procedure.

While particular detailed description has been herein provided for particular embodiments and variations according to the present invention, it is further understood that various modifications and improvements may be made by one of ordinary skill according to this disclosure and without departing from the broad scope of the invention.

What is claimed is:

1. A tissue ablation device assembly for ablating a substantial portion of a circumferential region of tissue at a location where a pulmonary vein extends from an atrium, comprising:

an elongate body with a proximal end portion and a distal end portion, the distal end portion having proximal and distal sections;

an expandable member including a proximal end and a distal end coupled to the proximal and distal sections of the distal end portion, respectively, the expandable member being adjustable between a radially collapsed condition and a radially expanded condition with an expanded outer diameter which is adapted to engage the substantial portion of the circumferential region of tissue; and an ultrasound ablation element secured to the distal section at a fixed position within the expandable member, wherein the ultrasound ablation element is adapted to emit a substantially circumferential pattern of ultrasound energy and to ablatively couple to the substantial portion of the circumferential region of tissue.

2. The assembly of claim 1, wherein the expanded outer diameter of the expandable member is at least 1.0 centimeters when in the expanded condition.

3. The assembly of claim 1, wherein the expanded outer diameter of the expandable member is at least 2.0 centimeters when in the expanded condition.

4. The assembly of claim 1, wherein the expanded outer diameter of the expandable member is between about 1.0 centimeter and about 2.5 centimeter when in the expanded condition.

5. The assembly of claim 1, wherein the distal end portion of the elongated body comprises a plurality of tubular members.

6. The assembly of claim 1, wherein the ultrasound ablation element comprises a substantially tubular ultrasound transducer that is mounted onto and surrounds the distal end portion at the fixed position.

7. The assembly of claim 6, wherein the distal end portion has an outer surface, and the ultrasound transducer is mounted onto the distal end portion with a radial separation between at least a portion of the ultrasound transducer and the outer surface of the distal end portion that forms a radial separation region with a gas-filled gap.

8. The assembly of claim 7, wherein the radial separation region is sealed to substantially prevent fluid from entering from outside of the radial separation region into the gap.

9. The assembly of claim 7, further comprising a support member being positioned within the radial separation region and bridging between the distal end portion of the elongated body and the tubular ultrasound transducer to thereby support at least in part the tubular ultrasound transducer around the distal end portion of the elongated body.

10. The assembly of claim 9, wherein the support member comprises a substantially elastomeric material.

11. The assembly of claim 7, wherein the distal end portion of the elongated body comprises a plurality of ridges that are spaced apart such that a plurality of said radial separation regions is formed within the spaces between the ridges and between tubular ultrasound transducer and the distal end portion.

12. The assembly of claim 6, wherein the tubular ultrasound transducer comprises a piezoceramic material and has an electrically conductive inner surface and an electrically conductive outer surface, and the assembly further comprising a first electrical lead with a distal end portion electrically coupled to the electrically conductive inner surface and a second electrical lead with a distal end portion electrically coupled to the electrically conductive outer surface, wherein each of the first and second electrical leads also has a proximal end portion terminating along the proximal end portion of the elongate body, and wherein the proximal end portions of the electrical leads are adapted to couple to an electrical current source.

13. The assembly of claim 1, wherein the ultrasound ablation element comprises an array of circumferentially spaced ultrasound transducer panels.

14. The assembly of claim 13, wherein each ultrasound transducer panel is adapted to be individually actuated, such that each ultrasound transducer panel is adapted to be ablatively couple to the substantial portion of the circumferential region of tissue.

15. The assembly of claim 14, wherein each of the circumferentially spaced ultrasound transducer panels in the array comprises a piezoceramic material, and further comprising a plurality of actuating lead assemblies, each of the actuating lead assemblies being coupled to a corresponding one of the ultrasound transducer panels in the array and also adapted to couple to an electrical current source.

16. The assembly of claim 1, wherein the ultrasound ablation element is adapted to ablatively couple simultaneously to the substantial portion of the circumferential region of tissue.

17. The assembly of claim 1, wherein the ultrasound ablation element is adapted to emit a continuous circumferential pattern of ultrasound energy whereby the entire circumferential region of tissue is ablated.

18. The assembly of claim 1, wherein the ultrasound ablation element is adapted to emit an acoustic signal at a frequency of between about 5 MHz to about 20 MHz.

19. The assembly of claim 1, wherein the ultrasound ablation element is adapted to emit an acoustic signal at a power level of at least about 20 Watts per centimeter radiator.

20. The assembly of claim 1, wherein the elongate body further comprises a tracking member that is adapted to slideably engage and track over a guide member positioned within the pulmonary vein.

21. The assembly of claim 1, further comprising at least one or more electrodes located along the distal end portion of the elongated body and disposed so as to contact tissue, said electrodes adapted to deliver and/or sense electrical signals to and from the tissue.

* * * * *